United States Patent [19]

Gante et al.

[11] 4,057,647
[45] Nov. 8, 1977

[54] ARALIPHATIC DIHALOGEN COMPOUNDS AND PROCESS FOR THEIR PREPARATION

[75] Inventors: Joachim Gante; Hans-Adolf Kurmeier; Dieter Orth; Erich Schacht; Albrecht Wild, all of Darmstadt, Germany

[73] Assignee: Merck Patent Gesellschaft mit beschrankter Haftung, Darmstadt, Germany

[21] Appl. No.: 695,804

[22] Filed: June 14, 1976

[30] Foreign Application Priority Data

June 28, 1975 Germany .............................. 2528958

[51] Int. Cl.$^2$ .................. A61K 31/045; A61K 31/085; C07C 31/02; C07C 43/20
[52] U.S. Cl. .............. 424/340; 260/429 AR; 260/410.5; 260/429.9; 260/618 D; 260/438.1; 260/613 R; 260/618 R; 424/308; 424/317; 424/343; 560/59; 560/60; 560/62; 560/255
[58] Field of Search .............................. 424/340, 343; 260/613 R, 618 R

[56] References Cited

U.S. PATENT DOCUMENTS

| 3,700,738 | 10/1972 | Bysouth et al. | 260/613 R |
| 3,801,654 | 4/1974 | Seeger et al. | 260/618 R |
| 3,859,256 | 1/1975 | Teufel et al. | 260/618 R |
| 3,969,418 | 7/1976 | Teufel et al. | 260/618 R |

*Primary Examiner*—Stanley J. Friedman
*Attorney, Agent, or Firm*—Millen & White

[57] ABSTRACT

Compounds of the formula

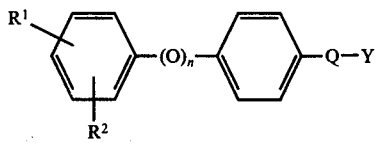

wherein
$R^1$ and $R^2$ are the same or different and are F, Cl or Br;
Q is $-CH(CH_3)-CH_2-$, $-C(OH)(CH_3)-CH_2-$ or $-C(CH_3)=CH-$;
Y is COOH, COOR$^3$, CH$_2$OH or CH$_2$OAc;
$n$ is 0 or 1;
$R^3$ is alkyl or aryl of up to 8 carbon atoms or $C_6H_4NHCOCH_3$; and
Ac is acyl of 1-8 carbon atoms;

and physiologically acceptable salts thereof, are anti-inflammatory agents, which can be made from compounds of the formula Z — X, wherein Z is

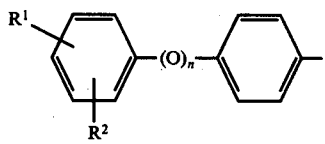

and X can be converted to —Q-Y.

20 Claims, No Drawings

ARALIPHATIC DIHALOGEN COMPOUNDS AND PROCESS FOR THEIR PREPARATION

BACKGROUND OF THE INVENTION

This invention relates to anti-inflammatory dihalodiphenyl ether compounds and dihalobiphenyl compounds.

SUMMARY OF THE INVENTION

In a compositional aspect, this invention relates to new araliphatic dihalogen compounds of Formula I

Z—Q—Y                I wherein Z is

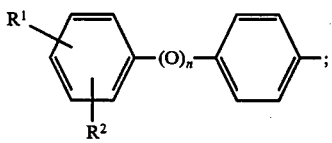

$R^1$ and $R^2$ are F, Cl or Br; Q is —CH(CH$_3$)-CH$_2$—, —C(OH) (CH$_3$)-CH$_2$— or —C(CH$_3$)=CH—; Y is COOH, COOR$^3$, CH$_2$OH or CH$_2$OAc; $n$ is 0 or 1; $R^3$ is alkyl or aryl of up to 8 carbon atoms or C$_6$H$_4$NHCOCH$_3$; and Ac is alkanoyl of 1–8 carbon atoms, and physiologically acceptable salts thereof.

In another compositional aspect, this invention relates to an anti-inflammatory pharmaceutical composition, comprising a compound of Formula I, in admixture with a pharmaceutically acceptable carrier.

In a method-of-use aspect, this invention relates to a method of relieving inflammation in a patient comprising administering to the patient an anti-inflammatorily effective amount of a compound of Formula I, in admixture with a pharmaceutically acceptable carrier.

In another compositional aspect, this invention relates to novel organometallic intermediates of Formula IIb Z—Q—M                IIb wherein Z and Q are as above and M is MgHal, ZnHal or one equivalent of an alkali metal, an alkaline earth metal, Cu, Cd or Zn and Hal is Cl, Br or I.

In another aspect, this invention relates to a process for the preparation of compounds of Formula I and physiologically acceptable salts thereof, wherein, a. in a compound of Formula II

Z—X                 II wherein Z is

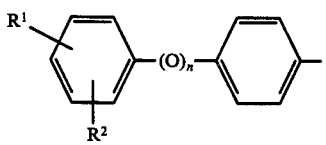

and X can be converted to —Q-Y and $R^1$, $R^2$, Q, $n$ and Y are as above, X is converted to —Q-Y;

b. a compound of Formula III

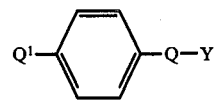

or a salt thereof is reacted with a compound of Formula IV

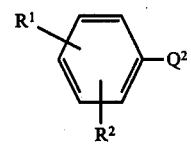

or with a salt thereof, and one of $Q^1$ and $Q^2$ is OH and the other is L; L is Hal, OH or a functionally-modified hydroxyl group; Hal is Cl, Br or I and $R^1$, $R^2$, Q and Y are as above;

c. or a compound of Formula V

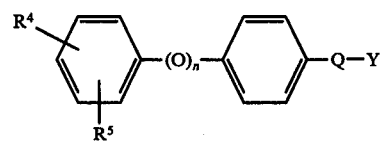

wherein $R^4$ is NH$_2$ or $R^1$, and $R^5$ is NH$_2$ or, if $R^4$ is NH$_2$, $R_5$ is $R^2$, and $R^1$, $R^2$, Q, $n$ and Y are as above, is diazotized and the diazonium salt is treated with a halogenating agent; and, optionally, one or more of Q and/or Y in a compound of Formula I is converted into one or more different Q and/or Y.

DETAILED DESCRIPTION

Compounds of Formula I include preferred biphenyl derivatives ($n$ is O) and diphenyl ether derivatives ($n$ is 1).

In the text, Z is

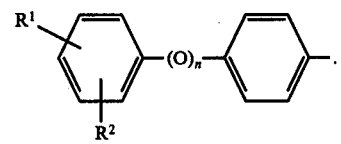

A is alkyl of 1-8, preferably 1-4 and, most preferably, 1 or 2 carbon atoms. Ar is aryl of up to 8 carbon atoms.

$R^1$ and $R^2$ are preferably the same and can be F, Cl or Br. F is preferred. The halogen substituents are preferably in the 2,4- or 3,4-positions of the phenyl ring but can also be in the 2,3-, 2,5-, 2,6- or 3,5-positions.

Z is preferably difluoro-4-biphenylyl, such as:

2′,4′-difluoro-4-biphenylyl,
3′,4′-difluoro-4-biphenylyl,
2′,3′-difluoro-4-biphenylyl,
2′,5′-difluoro-4-biphenylyl,
2′,6′-difluoro-4-biphenyl or
3′,5′-difluoro-4-biphenylyl;

dichloro-4-biphenylyl, such as:

2′,4′-dichloro-4-biphenylyl,
3′,4′-dichloro-4-biphenylyl,

2',3'-dichloro-4-biphenylyl,
2',5'-dichloro-4-biphenylyl,
2',6'-dichloro-4-biphenylyl or
3',5'-dichloro-4-biphenylyl;

dibromo-4-biphenylyl, such as:

2',4'-dibromo-4-biphenylyl,
3', 4'-dibromo-4-biphenylyl,
2',3'-dibromo-4-biphenylyl,
2',5'-dibromo-4-biphenylyl,
2',6'-dibromo-4 -biphenylyl or
3',5'-dibromo-4-biphenylyl;

4-(difluorophenoxy)-phenyl, such as:

4-(2,4-difluorophenoxy)phenyl,
4-(3,4-difluorophenoxy)phenyl,
4-(2,3-difluorophenoxy)phenyl,
4-(2,5-difluorophenoxy)phenyl,
4-(2,6-difluorophenoxy)phenyl or
4-(3,5-difluorophenoxy)phenyl;

4-(dichlorophenoxy)phenyl, such as:

4-(2,4-dichlorophenoxy)phenyl,
4-(3,4-dichlorophenoxy)phenyl,
4-(2,3-dichlorophenoxy)phenyl,
4-(2,5-dichlorophenoxy)phenyl,
4-(2,6-dichlorophenoxy)phenyl or
4-(3,5-dichlorophenoxy)phenyl; or 4-(dibromophenoxy)phenyl, such as:

4-(2,4-dibromophenoxy)phenyl,
4-(3,4-dibromophenoxy)phenyl,
4-(2,3-dibromophenoxy)phenyl,
4-(2,5-dibromophenoxy)phenyl,
4-(2,6-dibromophenoxy)phenyl or
4-(3,5-dibromophenoxy)phenyl.

However, $R^1$ and $R^2$ in Z can differ from one another, for example, Z can be chlorofluoro-4-biphenylyl, such as 2'-chloro-4'-fluoro-4-biphenylyl or 2'-fluoro-4'-chloro-4-biphenylyl; or 4-(chlorofluorophenoxy)phenyl such as 4-(2-chloro-4-fluorophenoxy)phenyl or 4-(2-fluoro-4-chlorophenoxy)phenyl.

Q is —CH(CH$_3$)-CH$_2$—, —C(OH)(CH$_2$—, or —C(CH$_3$)=CH—, but preferably is —C(OH) (CH$_3$)-CH$_2$—.

$R^3$ is A or Ar, each of up to 8 carbon atoms. A is preferably methyl or ethyl, but can also be, for example, n-propyl, isopropyl, n-butyl, isobutyl, sec.-butyl, tert.-butyl, n-pentyl, isopentyl, n-hexyl, n-heptyl, n-octyl or 2-ethylhexyl. Ar is preferably phenyl, o-, m- or p-tolyl or o-, m- or, most preferably, p-acetamidophenyl.

Ac is preferably acetyl, but can also be, for example, formyl, propionyl, butyryl, isobutyryl, valeryl, isovaleryl, trimethylacetyl, capronyl, isocapronyl, tert.-butylacetyl, heptanoyl, octanoyl, as well as benzoyl, nicotinoyl or isonicotinoyl. Y is preferably COOH, COOCH$_3$, COOC$_2$H$_5$, COO-p-C$_6$H$_4$-NHCOCH$_3$ or CH$_2$OH.

Preferred compounds of Formula I are those in which at least one of the substituents or functions is preferred. Among preferred compounds of Formula I are those wherein:
a. n is 0;
b. n is 1;
c. $R^1$ and $R^2$ are F, including (a)-(b);
d. Y is COOH, including (a)-(c);
e. Y is COOCH$_3$, including (a)-(c);
f. Y is COOC$_2$H$_5$, including (a)-(c);
g. Y is COO-C$_6$H$_4$-NHCOCH$_3$, including (a)-(c);
h. Y is CH$_2$OH, including (a)-(c);
i. Z is 2', 4'-difluoro-4-biphenylyl, 2',4'-dichloro-4-biphenylyl, 3',4'-dichloro-4-biphenylyl, 2',4'-dibromo-4-biphenylyl, 4-(2,4-difluorophenoxy)phenyl, 4-(2,4-dichloro-phenoxy)phenyl or 4-(2-fluoro-4-chlorophenoxy)phenyl;
j. Z is 2',4'-difluoro-4-biphenylyl, 2',4'-dichloro-4-biphenylyl, 3',4'-dichloro-4-biphenylyl, 2',4'-dibromo-4-biphenylyl, 4-(2,4-difluorophenoxy)phenyl, 4-(2,4-dichloro-phenoxy)phenyl or 4-(2-fluoro-4-chlorophenoxy)phenyl, including (a)-(h);
k. Z is 2',4'-difluoro-4-biphenylyl, 2',4'-dichloro-4-biphenylyl, 4-(2,4-difluorophenoxy)phenyl, or 4-(2,4-dichlorophenoxy)phenyl, including (a)-(h);
l. Z is 2',4'-difluoro-4-biphenylyl, 2',4'-dichloro-4-biphenylyl, 4-(2,4-difluorophenoxy)phenyl or 4-(2,4-dichlorophenoxy)phenyl, including (a)-(h);
m. Z is 2',4'-difluoro-4-biphenylyl, including (a)-(h);
n. Z is 2',4'-difluoro-4-biphenylyl and Y is COOH, COOCH$_3$, COOC$_2$H$_5$, COO-p-C$_6$H$_4$-NHCOCH$_3$ or CH$_2$OH, including (a)-(h);
o. Q is —CH(CH$_3$)-CH$_2$—, including (a)-(n);
p. Q is —C(OH)(CH$_3$)-CH$_2$—, including (a)-(n); and
q. Q is —C(CH$_3$)=CH—, including (a)-(n).

In the specification, unless expressly indicated otherwise, $R^1$, $R^2$, Q, Y, n, $R^3$, Ac, Z, X, $Q^1$, $Q^2$, L, Hal, $R^4$ and $R^5$ are as indicated for Formulae I to V.

Preparation of compounds of Formula I is carried out by known methods, as described in the literature, for example, in standard reference works, such as Houben-Weyl, Methoden der organischen Chemie (Methods of Organic Chemistry), Georg-Thieme-Verlag, Stuttgart, and Organic Reactions, John Wiley & Sons, Inc., New York, under reaction conditions known as suitable. It is also possible to use known variants not described in more detail here.

Some of the starting materials of Formulae II, III, IV and V are known and some are new. They can be prepared by known methods and, if desired, can be prepared in situ, and be immediately reacted further to give compounds of Formula I.

Compounds of Formula I are preferably prepared by
a. treating a compound of Formula IIa

   IIa wherein $X^1$ is a group which can be solvolyzed to the —Q-Y, with a solvolyzing agent, or b. reacting a compound of Formula IIb

   IIb wherein M is MgHal, ZnHal or one equivalent of a metal atom or of an organometallic radical, with a compound of Formula VI

   VI wherein $R^6$ is H$_2$ or O, or with a reactive derivative thereof, or c. treating a compound of Formula IIc $$Z-X^2 \quad \text{IIc}$$

wherein $X^2$ is a group which can be reduced to —Q-Y, with a reducing agent, or d. splitting a compound of Formula IId $$Z-X^3 \quad \text{IId}$$

wherein $X^3$ corresponds to the —Q-Y but additionally contains a group which can be removed thermolytically, or e. reacting a compound of Formula IIe $$Z-Q-L \quad \text{IIe}$$

or a de-HL derivative thereof with CO and/or a metal carbonyl, if appropriate in the presence of a catalyst.

Compounds I are obtainable, preferably, by solvolysis, preferably hydrolysis, of corresponding functionally-modified compounds of Formula IIa.

In Formula IIa, $X^1$ is preferably —CE($CH_3$)-$CH_2$-Y, —CE($CH_3$)-CH[P=O($OR^7$)$_2$]-Y, —CH($CH_3$)-C(=$PAr_3$)-Y, —CH($CH_3$)-CH(CO-$R^7$)-Y or —Q-W, wherein E is Hal or a functionally-modified hydroxyl, $R^7$ is alkyl, aryl or aralkyl of up to 12 carbon atoms, preferably A, phenyl or benzyl, and W is functionally-modified COOH or $CH_2OH$, which differs from Y.

Solvolysis of these substances proceeds successfully in acid, neutral or alkaline media at temperatures between about −20° and 300°, preferably 0° and 120°. Acid catalysts used for the solvolysis are preferably hydrochloric acid, hydrobromic acid, sulfuric acid, acetic acid or acid salts, such as $NH_4Cl$. Basic catalysts include sodium hydroxide, potassium hydroxide, calcium hydroxide or barium hydroxide, sodium carbonate or potassium carbonate. Solvents are preferably water; lower alcohols, such as methanol, ethanol or hexanol; ethers, such as diethyl ether, tetrahydrofuran (THF) or dioxane; amides, such as dimethylformamide (DMF); nitriles, such as acetonitrile; ketones, such as acetone; sulfones, such as tetramethylene-sulfone; hydrocarbons, such as benzene or toluene; or mixtures of these solvents, preferably mixtures containing water.

Solvolysis of alcohol derivatives of the formula Z-CE($CH_3$)-$CH_2$-Y is preferred. In these derivatives, E is, preferably, a functionally-modified OH group or Cl, Br or I. The OH group can, for example, be functionally modified in the form of an alcoholate, preferably a zinc alcoholate of the formula Z-C($CH_3$)(OZnHal)-$CH_2$-Y, most preferably, Z-C($CH_3$)(OZnHal)-$CH_2$-$COOR^3$. These compounds are formed as primary products in syntheses with zinc-organic compounds, especially the Reformatsky reaction. Other alcoholates include magnesium or lithium alcoholates, which are formed by Grignard reactions or reactions with organolithium compounds. Esters, for example, carboxylic acid esters in which the alkanoyl is of up to 7 carbon atoms, for example, acetyl or benzoyl; alkylsulfonic or arylsulfonic acid esters, wherein the alkyl is of 1 to 6 carbon atoms and aryl is of 6 to 10 carbon atoms; ethers, for example, alkyl ethers, wherein alkyl is of up to 6 carbon atoms; aryl ethers, where aryl is of 6 to 10 carbon atoms; aralkyl ethers, wherein aralkyl is of 7 to 11 carbon atoms, can be used. Boric acid esters formed as intermediates during oxidative hydroborination can also be used.

Compounds of the formula Z-C($CH_3$)(OZnHal)-$CH_2$-$COOR^3$ are preferably obtained by reacting ketones of formula Z-CO-$CH_3$ with organo-zinc compounds of formula HalZn-$CH_2COOR^3$ under Reformatsky synthesis conditions, (see, Organic Reactions, volume 1, page 1 et seq.). The ketones are obtainable, for example, by Friedel-Crafts acetylation of corresponding compounds of formula Z-H. Organo-zinc compounds are preferably prepared in situ from the appropriate halogenoacetic acid derivatives and zinc. Preferred halogenoacetic acid derivatives are bromoacetic acid esters, especially methyl and ethyl bromoacetate.

The reaction can also be carried out with bromoacetic acid, which preferably is converted into a salt $BrCH_2$-COOZnBr using allyl-zinc bromide. The zinc can be employed in any desired form, for example, zinc dust, zinc foil, zinc wool or zinc granules. The reaction can be carried out in the absence or, preferably, in the presence of a solvent. Examples of suitable solvents include hydrocarbons, such as benzene or toluene; ethers, such as diethyl ether, THF, methylal or dioxane; and mixtures thereof. Addition of iodine or trimethyl borate can be advantageous.

Reaction temperatures are between about 0° and about 150°, preferably between 20° and the boiling point of the solvent. The resulting zinc complex can be hydrolyzed to alkyl esters of Formula I (Y is COOA). Under more vigorous hydrolysis conditions, the esters are saponified, in the reaction mixture, to acids I (Y is COOH). Water can be eliminated during hydrolysis under more stringent conditions so that unsaturated compounds I, Q is —C($CH_3$)=CH—, are formed in addition to, or instead of, the hydroxy acid derivatives I, Q is —C(OH)($CH_3$)-$CH_2$—.

It is also possible to react organo-lithium compounds or Grignard compounds M-$CH_2$-Y (M is Li or MgHal) with ketones Z-CO-$CH_3$ under the same or similar conditions. Metal alcoholates Z-C($CH_3$)(OM)-$CH_2$-Y are formed.

Metal alcoholates Z-C($CH_3$)(OM)-$CH_2$-Y (M is Li or MgHal) are also obtainable by reacting ketones Z-CO-$CH_2$-Y with organometallic compounds $CH_3$-M (M is Li or MgHal), such as methyllithium, methylmagnesium bromide or methyl magnesium iodide, or by reacting ketones $CH_3$-CO-$CH_2$-Y with organometallic compounds Z-M (M is Li or MgHal).

Ketones of the formula Z-CO-$CH_2$-$COOR^3$ are obtainable by brominating ketones Z-CO-$CH_3$, reacting the products with KCN to give ketonitriles Z-CO-$CH_2$-CN, hydrolyzing the ketonitriles and optionally esterifying the reaction product. Ketones Z-CO-$CH_2$-$CH_2$-OH and their acylates can be prepared by reacting compounds ZH with acid chlorides Cl-CO-$CH_2$-$CH_2$-L and, if necessary, subsequently hydrolyzing the reaction product. Grignard reactions and reactions with organolithium compounds are preferably carried out under conditions the same as, or similar to, those for the Reformatsky reaction.

Metal alcoholates of the formula Z-C($CH_3$)(OM)-$CH_2$-Y (M is Li, MgHal or ZnHal), are preferably not isolated but, after their formation, are hydrolyzed in situ with dilute acids, for example, sulfuric acid or hydrochloric acid, or with an aqueous ammonium chloride solution. Compounds of Formula I are formed.

One variant of the above reactions is reacting a ketone Z-CO-$CH_3$ with an alkoxyethinylmetallic compound AO-C≡C-M, for example, ethoxy-ethinyl-magnesium bromide. The carbinol Z-C($CH_3$)(OH)-C≡C-OA, which is obtained by hydrolysis can be rearranged, by solvolysis in a weakly acid medium, for example, with solid $CO_2$ in ethanol, to the corresponding unsaturated ester $Z-C(CH_3)=CH-COOA$.

Compounds of formulae $Z-CE(CH_3)-CH_2-Y$ and $Z-Q-CH_2-E$, wherein E is Cl, Br, I or an acylated OH group, are preferably saponified in an aqueous or aqueous-alcoholic solution or suspension, if desired, with addition of a solubilizing agent, for example, an alcohol, glycol or glycol ether. The saponifying agents are preferably alkali metal hydroxides, such as NaOH or KOH; alkaline earth metal hydroxides, such as $Ca(OH)_2$ or $Ba(OH)_2$; or suspensions of $Pb(OH)_2$ or AgOH. The solvents are preferably alcohols, such as methanol, ethanol and isopropanol, or mixtures thereof with water. The saponification is carried out at temperatures between about 20° and 100°, preferably between 60° and 100°. These compounds can also be hydrolyzed by water, preferably in the presence of catalytically active amounts of a mineral acid, such as sulfuric acid, preferably at temperatures between 20° and 100°, most preferably between 40° and 60°.

If E is etherified OH, it is appropriately split by a hydrogen halide acid, such as HBr or HI. The reaction is advantageously carried out in acetic acid or aqueous acetic acid at temperatures between 60° and the boiling point, preferably, at the boiling point. Usually, the resulting halogen compounds are hydrolyzed with alcoholic alkali.

Starting materials of the formula $Z-CE(CH_3)-CH[P=O(OR^7)_2]-Y$ can be obtained by converting a phosphonic acid ester $(R^7O)_2P(=O)-CH_2COOR^3$ to the corresponding metal derivative using a strong base, for example, an alkali metal alcoholate or a lithium dialkylamide, such as lithium diisopropylamide, and reacting the metal derivative with a ketone $Z-CO-CH_3$. The resulting intermediate, in which E is OM and M is a metal atom from the strong base used, for example, Na or Li, is usually hydrolyzed under very mild conditions, for example, with dilute acetic acid at temperatures between 0° and 20°. Unsaturated compounds of the formula $X-C(CH_3)=CH-Y$ are formed, with elimination of ester salts of phosphoric acid. In this reaction, the nature of $R^7$ is not critical because it does not remain in the reaction product.

Starting materials of the formula $Z-CH(CH_3)-C(=PAr_3)-Y$ can be obtained by reacting halides $Z-CH(CH_3)-Hal$, wherein Hal is preferably Br, with triarylphosphoranes $Ar_3P=CH-Y$, preferably triarylphosphoranylideneacetic acid alkyl esters $Ar_3P=CH-COOA$, for example, triphenylphosphoranylideneacetic acid ethyl ester. Heating in an inert solvent, such as ethyl acetate, is preferred. The intermediate can be hydrolyzed with strong bases, such as sodium hydroxide solution or potassium hydroxide solution, in aqueous alcohols, for example, aqueous methanol, preferably at temperatures between 40° and 100°. The nature of Ar, which is eliminated during the reaction as the corresponding triarylphosphine oxide, is not critical.

Compounds of Formula I are also obtainable by acidic cleavage of keto compounds $Z-CH(CH_3)-CH(COR^7)-Y$, especially ketoesters $Z-CH(CH_3)-CH(COR^7)-COOR^3$. These are obtained, for example, by reacting a halide $Z-CH(CH_3)-Hal$ with a ketoester $R^7-CO-CH_2-COOR^3$, preferably an acetoacetic acid alkyl ester or benzoylacetic acid alkyl ester, and, if desired, saponifying the reaction product. During acid scission, one mole of $R^7-COOA$ is split off. The nature of $R^7$ is not critical, but is preferably methyl or phenyl.

Acid scission is generally effected by treatment with a strong base, such as NaOH, KOH or $Ca(OH)_2$, in solvents such as water; lower alcohols, such as methanol or ethanol; ethers, such as diethyl ether, THF or dioxane; hydrocarbons, such as benzene; or mixtures thereof at temperatures between about $-10°$ and 200°. If free carboxylic acids of Formula I (Y is COOH) are desired, the reaction mixture is preferably heated to temperatures between about 60° and 100° for several hours, if desired, under an inert gas, e.g., nitrogen.

Compounds of Formula I can also be prepared by solvolysis of acid derivatives Z-Q-W. W is one of the following, wherein the group being eliminated, i.e., R' and R", can be any desired radicals, including alkyl of 1–4 carbon atoms and can be identical or different and collectively can be, for example, tetramethylene or pentamethylene, optionally interrupted by O: $CHal_3$; COOR''', wherein R''' is different from $R^3$, preferably alkyl of 9 to 12 carbon atoms or substituted alkyl; $C(OR')_3$; COOAcyl, wherein Acyl is the alkanoyl function of a carboxylic acid of up to 17 carbon atoms, preferably an alkanoyl of the formula Z-Q-CO—; CN; $CONH_2$; CONHR'; CONR'R"; CONHOH; $C(OH)=NOH$; $CONHNH_2$; $CON_3$; $C(OR')=NH$; $C(NH_2)=NNH_2$; $C(NHNH_2)=NH$; CSOH; COSH; CSOR; $CSNH_2$; CSNHR'; CSNR'R"; or $CH_2E$. Preferably, W is nitrile or acid amide. Compounds of the formula Z-Q-W are obtainable in a known manner, for example, by reacting ketones $Z-CO-CH_3$ with compounds $M-CH_2-W$ and subsequently hydrolyzing the reaction products. If desired, the resulting products can be dehydrated and/or reduced. Nitriles of the formula Z-Q-CN can also be obtained from corresponding halides Z-Q-Hal by reaction with KCN. The acid amides and imino-esters can be obtained by partial hydrolysis or alcoholysis of the nitriles.

Nitriles of the formula Z-Q-CN and amides of the formulae $Z-Q-CONH_2$, Z-Q-CONHR' or Z-Q-CONR'R" are preferably hydrolyzed in a strongly alkaline or strongly acid medium, for example, aqueous-alcoholic alkali, preferably at temperatures between 60° and 160°. Treatment of imino-ether hydrochlorides $Z-Q-C(OA)=NH.HCl$ with hot water yields esters Z-Q-COOA.

Halogen atoms in compounds of the formula $Z-Q-CH_2Hal$ can also be replaced, by treatment with fatty acid salts, for example, potassium acetate or heavy metal acetates, in inert solvents, such as dimethylformamide, at temperatures between about 20° and about 100°, by the corresponding alkanoyloxy groups.

Halogen atoms or ester groups bonded to the tertiary carbon atom of $Z-CE(CH_3)-CH_2-Y$ can also be replaced by OH, or split, by treatment with water, preferably in the presence of catalytically active amounts of a mineral acid such as sulfuric acid, at temperatures of between 20° and 100°, preferably 40° to 60°.

Primary amines $Z-Q-CH_2NH_2$ can be diazotized and hydrolyzed by warming in an acid aqueous solution. Alcohols $Z-Q-CH_2OH$ are formed.

Etherified OH groups are preferably split by a hydrogen halide acid such as HBr or HI. The reaction is advantageously carried out in acetic acid or aqueous acetic acid at temperatures between 60° and the boiling point, preferably at the boiling point. Usually the resulting halogen compounds are subsequently hydrolyzed with alcoholic alkali.

Compounds of Formula I are also obtainable by reacting organometallic compounds of Formula IIb with carbon dioxide or formaldehyde or with reactive derivatives thereof, for example, chloroformic acid esters CLCOOA, orthocarbonic acid esters C(OA)$_4$, dialkylcarbonates and diarylcarbonates, paraformaldehyde or formaldehyde-acetals. In compounds IIb, M is MgCl, MgBr, MgI, ZnCl, ZnBr or ZnI, or preferably, one equivalent of an alkali metal, for example, Li, Na or K; an alkaline earth metal, for example, Mg or Ca; or Cu, Cd or Zn. The reaction proceeds under known conditions for synthesis with organometallic compounds. Starting materials of Formula IIb are new and obtainable, for example, by reacting ketones Z-CO-CH$_3$ with organometallic compounds CH$_3$-M and hydrolyzing the reaction products to give carbinols Z-C(OH)(CH$_3$)$_2$, eliminating water to give olefin derivatives Z-C(CH$_3$)=CH$_2$, carrying out oxidative hydroboration and hydrolysis to give alcohols Z-CH(CH$_3$)-CH$_2$OH and reacting the latter with PBr$_3$ and then with Mg or Li. Starting materials of Formula VI and their derivatives are known or can be prepared in a known manner.

Examples of suitable solvents for the reaction of IIb with VI or VI derivatives are ethers, such as diethyl ether, diisopropyl ether, 1,2-dimethoxyethane, THF or dioxane; mixtures thereof with one another or with hydrocarbons such as hexane, benzene, toluene or xylene; amides, such as DMF or hexamethylphosphoric acid triamide; and sulfoxides, such as dimethylsulfoxide (DMSO). Reaction temperatures are between about −20° and 180°, preferably between 0° and 70°. The reaction times vary between 0.5 and 72 hours.

Carboxylic acids Z-Q-COOH are obtained by reacting compounds Z-Q-M with CO$_2$. For this purpose, a stream of dry CO$_2$ can be passed into a cooled solution of organometallic compound or this solution can be poured onto solid CO$_2$. Preferably, the Grignard compounds Z-Q-MgHal, which are prepared using a large excess of a mixture of magnesium filings and magnesium powder, are used and a vigorous stream of CO$_2$ is passed through the reaction mixture while the Grignard compound is being prepared.

Compounds of Formula I are obtainable by reducing compounds of Formula IIc. $X^2$ is preferably —$X^5$-Y, and $X^5$ is a group which can be reduced to Q. $X^5$ is particularly —C(=CH$_2$)-CH$_2$—, —CR$^8$(CH$_3$)-CH$_2$—, —CH(CH$_3$)-CHR$^9$—, —C(OH)(CH$_3$)-CHR$^9$—, —C(CH$_3$)=CR$^9$— or —CR$^8$(CH$_3$)-CHR$^9$—, wherein R$^8$ and R$^9$ in each case are radicals which can be removed by reduction, preferably, OH, OAc, Hal, SH, NH$_2$ or aralkyloxy or aralkylamino of up to 10 carbon atoms. $X^2$ can be —Q-Y$^1$ or —X$^5$-Y$^1$, wherein Y$^1$ is a group which can be reduced to Y, preferably to CH$_2$OH. Y$^1$ is preferably CHO, functionally-modified COOH or CHO group which differs from Y, or benzyloxymethyl. Examples of compounds of Formula IIc are carboxylic acids Z-C(=CH$_2$)-CH$_2$-COOH, Z-CCl(CH$_3$)-CH$_2$COOH, Z-CH(CH$_3$)-CHCl-COOH, Z-C(OH)(CH$_3$)-CHCl-COOH, Z-C(CH$_3$)=CCl-COOH and Z-C(CH$_3$)Cl-CHCl-COOH, alkyl esters thereof and the corresponding carbinols (CH$_2$OH instead of COOH) and their alkanoyl esters, aldehydes Z-Q-CHO and benzyl ethers Z-Q-CH$_2$OCH$_2$C$_6$H$_5$.

Reduction of these starting materials is preferably effected by catalytic hydrogenation or chemically.

Examples of catalysts for catalytic hydrogenations are noble metal catalysts, nickel catalysts, cobalt catalysts and mixed catalysts, such as copper chromium oxide. Noble metals which can be used are, preferably, platinum or palladium, which can be supported, for example, on charcoal, calcium carbonate or strontium carbonate, or in the form of oxides or as finely divided metal. Nickel and cobalt are preferably used in the form of Raney catalysts. The hydrogenation can be carried out at pressures between about 1 and 100 atmospheres, at temperatures between about −80° and +150°, preferably between 20° and 100°. The hydrogenation is carried out in an inert solvent, for example, alcohol, such as methanol, ethanol or isopropanol; a carboxylic acid, such as acetic acid; an ester, such as ethyl acetate; or an ether, such as THF or dioxane. Solvent mixtures, including mixtures containing water, can also be used.

Another method for reducing compounds IIc is reaction with nascent hydrogen, which can be produced by treating metals with acids or bases. It is possible to use, zinc/acid, zinc/alkali metal hydroxide solution, iron/acid or tin/acid systems. Examples of suitable acids are hydrochloric acid or acetic acid. An aluminum/nickel alloy in an alkaline aqueous solution, optionally with addition of methanol, or sodium or aluminum amalgam in an aqueous alcoholic or aqueous solution are also suitable to produce nascent hydrogen. The reduction is carried out at temperatures between 0° and 150°, preferably between 20° and the boiling point of the solvent used.

If alcohols of the formula Z-Q-CH$_2$OH are being prepared, complex metal hydrides such as LiAlH$_4$ or NaBH$_4$ or sodium aluminum bis-(alkoxyalkoxy)-dihydrides, such as NaAl(OCH$_2$CH$_2$OCH$_3$)$_2$H$_2$, as well as diborane, optionally with the addition of catalysts such as BF$_3$, AlCl$_3$ or LiBr, can be used as reducing agents. Solvents for this reaction are preferably ethers such as diethyl ether, THF, dioxane, 1,2-dimethoxyethane or diglyme. Solvents for reduction with NaBH$_4$ are preferably alcohols such as methanol or ethanol. The reduction is preferably carried out at temperatures between about −80° and +150°, most preferably between about 20° and 120°.

Another suitable reducing agent is tin(II)chloride, which is used, preferably, in the form of the dihydrate in aqueous, aqueous-alcoholic or acid aqueous solution, for example, in the presence of acetic acid and/or hydrochloric acid, at temperatures between about 0° and 120°.

Another reducing agent is hydriodic acid. Phosphorus and/or solvents, such as acetic acid, are optional additives. Temperatures between 100° and the boiling point are preferred. It is also possible to produce hydrogen iodide in situ by, for example, using a mixture of KI, red phosphorus and phosphoris acid as reducing agent, preferably at temperatures between 100° and 150°.

Other suitable reducing agents are, for example, sodium dithionite in alkaline or ammoniacal solution; iron-(II)hydroxide; hydrogen sulfide and its derivatives, preferably metal bisulfides, metal sulfides and metal polysulfides; and SO$_2$ and its derivatives, for example, bisulfites and sulfites. It is also possible to reduce carbonyl to CH$_2$ in compounds of Formula IIc, by the Clemmensen or Wolf-Kishner methods.

Using the methods given, it is possible to reduce several reducible groups in a given starting material, the reaction proceeding via compounds of Formula IIc, which are formed as intermediates but need no be isolated. It is also possible simultaneously to reduce Q, which is present in the starting material, to a different Q.

Compounds of Formula I are also obtainable by thermolysis of compounds of Formula IId.

Additional, thermolytically removable groups in $X^3$ are, preferably carboxyl groups, which can be removed by decarboxylation.

Starting compounds which are suitable for decarboxylation correspond to the formula Z-$X^6$(COOH)-Y, wherein $X^6$ is —CH($CH_3$)-CH<, —C(OH)($CH_3$)-CH< or —C($CH_3$)=C< and Y is preferably COOH or COO$R^3$. Malonic acid derivatives of this type are obtainable by condensation of ketones Z-CO-$CH_3$ with a malonic acid dialkyl ester and, if desired, subsequent hydrogenation of the product. Diesters of formula Z-$H^6$=(COOA)$_2$ thus obtained can subsequently be saponified completely or partially.

As described in the literature, the decarboxylation can be carried out by dry heating until the evolution of $CO_2$ has ceased, under reduced pressure, or by warming in solvents such as water, ethanol, dioxane or xylene, to temperatures between 50 and 300°. It is also possible to split off $CO_2$ by heating with acids, for example, a mixture of aqueous hydrochloric acid and acetic acid, if desired under an inert gas, such as nitrogen.

Compounds of Formula I are also obtainable by carbonylation of compounds of Formula IIe or of their de-HL derivatives, if appropriate, in the presence of a catalyst.

Suitable starting materials for the carbonylation are compounds of the formulae Z-Q-Cl, Z-Q-Br, Z-Q-I, Z-Q-OH and Z-C($CH_3$)=$CH_2$.

As described in the literature, the carbonylation can be carried out by reaction with gaseous CO, preferably under pressures up to 700 atmospheres and at temperatures up to 300°, using a heavy metal catalyst. It is also possible to react CO in the form of a heavy metal carbonyl with a starting material of Formula IIe. It is possible to produce the CO, required for the carbonylation, in situ from a mixture of formic acid and a mineral acid, especially concentrated sulfuric acid.

The following are typical process variants for the carbonylation reaction:

Compounds of Formula IIe, can preferably be reacted with a heavy metal carbonyl, e.g., nickel carbonyl. In one embodiment, halogen derivatives Z-Q-Hal are preferably used as starting material. An alkali metal tert.-alcoholate is added as catalyst and the reaction is carried out in a lower tert.-alkanol solvent. Tert.-butanol is preferred as solvent. Suitable alkali metal alcoholates are, in particular, sodium, potassium and lithium derivatives of tert.-alkanols, such as sodium tert.-butylate, potassium tert.-butylate and lithium tert.-butylate. Reaction temperatures are between about 0° and 120°, preferably between 30° and 100°. Reactions times are between 1 hour and about 4 days. Tert.-Alkyl esters Z-Q-COO-tert.-alkyl are obtained. These need not be isolated, but can be saponified in situ to the free acids.

In another embodiment, compounds IIe, preferably Z-C($CH_3$)=$CH_2$ or Z-Q-OH, are reacted with a heavy metal carbonyl, preferably nickel carbonyl, preferably in an inert solvent, such as THF, dioxane or acetone, in the presence of water. An inorganic acid such as HCl, $H_2SO_4$, HBr, HI or $H_3PO_4$ can be present. Reaction temperatures are between about 20° and about 100°. The reaction can be accelerated by irradiation, for example, with a mercury vapor lamp. A period of about 2 hours to about 2 days is required for the reaction.

When formic acid/sulfuric acid is used as the carbonylating reagent, vinyl compounds Z-C($CH_3$)=$CH_2$ or carbinols Z-Q-OH are preferably used as starting materials. The starting materials are reacted at temperatures of 0° –40° with a mixture of formic acid and concentrated sulfuric acid. The mixture can contain 0–50% of acetic or trifluoroacetic acid.

Carbonylation with gaseous CO is preferably carried out under a pressure of 100 to 700 atmospheres in an inert solvent, preferably in a lower alcohol, such as methanol, ethanol, propanol, isopropanol, n-butanol, n-pentanol or n-hexanol; or a cycloalkanol, such as cyclohexanol. Suitable catalysts are, for example, nickel carbonyl or a nickel halide; cobalt carbonyl or cobalt halide; palladium chloride; rhodium trichloride and bis-triphenyl-phosphine-palladium dichloride.

Compounds of Formula I can also be obtained by reacting a compound of Formula III, or a salt thereof, with a compound of Formula IV or a salt thereof. Starting materials of Formula III are obtainable, for example, by reacting p-$Q^1$-acetonphenones with bromoacetic acid alkyl esters and zinc and optionally subsequently saponifying and/or dehydrating and/or reducing the reaction products. Most of the starting materials of Formula IV are known.

A phenol of Formula III ($Q^1$ is OH) can be reacted with a compound of Formula IV ($Q^2$ is L) or a compound of Formula III ($Q^1$ is L) with a phenol of Formula IV ($Q^2$ is OH). The phenols are preferably in the form of the corresponding phenolates, preferably the sodium or potassium phenolate. The reaction is preferably carried out in an inert solvent, such as DMF or phosphoric acid hexamethyl triamide (HMPT), in the presence of a catalyst, e.g., copper powder, at temperatures between about 50° and 200°, preferably between 80° and 130°.

Compounds of Formula I can also be obtained from corresponding amino compounds of Formula V by diazotizing the latter, for example, with salts or esters of nitrous acid, such as $NaNO_2$ or n-butyl nitrite, in aqueous hydrochloric acid at temperatures between about −20° and +10° and converting the resulting diazonium salt to the halogen compound. Fluorine compounds (I, $R^1$ and/or $R^2$ is F) are preferably obtained by reacting diazonium salts with $HBF_4$ to give diazonium tetrafluoborates and subjecting these to thermal decomposition at about 100°–200° with or without an inert solvent such as toluene, xylene or dioxane. Decomposition at room temperature in an aqueous medium in the presence of copper powder is also possible. If the diazotization is carried out with $NaNO_2$ in anhydrous hydrofluoric acid, the desired fluorine compound is obtained directly by subsequent warming. Exchange of the diazonium group by chlorine or bromine is preferably carried out in a hot aqueous solution in the presence of $Cu_2Cl_2$ or $Cu_2Br_2$. Starting materials of Formula V are obtainable, for example, by reducing corresponding compounds containing one or two nitro groups instead of $R^5$ and/or $R^6$.

One or both of Q and/or Y in a product of Formula I can optionally be converted to an other Q and/or Y.

It is possible to convert one Y to another Y, for example, by treating the product with reducing, oxidizing, solvolyzing, esterifying, transesterifying or salt-forming agents.

Thus, for example, an acid of formula Z-Q-COOH or an ester of formula Z-Q-COO$R^3$ or Z-Q-$CH_2$OAc can be reduced to the corresponding alcohol Z-Q-$CH_2$OH. The reduction is preferably carried out with a complex metal hydride, such as LiAl$H_4$, by methods indicated above. Conversely, it is possible to oxidize an alcohol of formula Z-Q-CH$_2$OH to the corresponding carboxylic acid Z-Q-COOH, for example, using KMnO$_4$, CrO$_3$ or Ag$_2$O.

Esters Z-Q-COOR$^3$ or Z-Q-CH$_2$Oac can be solvolyzed, and, preferably, hydrolyzed, to free carboxylic acids Z-Q-COOH or alcohols Z-Q-CH$_2$OH. The solvolysis or hydrolysis (saponification) of these esters is generally carried out under conditions indicated above for solvolysis of compounds of Formula IIa. Preferably, the esters are treated for about 1-48 hours with NaOH, KOH or K$_2$CO$_3$ in methanol, ethanol or isopropanol at temperatures between about 20° and 120°. It is also possible to carry out the hydrolysis under acid conditions, for example, with acetic/hydrochloric acid at about 20°-120°, or under neutral conditions, with water at about 100°-200°, if desired under pressure.

An acid of formula Z-Q-COOH can be esterified with an alcohol A-OH or a phenol Ar-OH, for example, in the presence of an inorganic or organic acid, such as HCl, HBr, HI, H$_2$SO$_4$, H$_3$PO$_4$, trifluoroacetic acid or a sulfonic acid, such as benzenesulfonic or p-toluenesulfonic acid, or of an acid ion exchange resin, optionally in the presence of an inert solvent, such as benzene, toluene or xylene, at temperatures between about 0° and about 140°. The alcohol is preferably used in excess. The water from the reaction can be removed as an azeotrope, by codistillation with a hydrocarbon, for example, benzene or toluene, or chlorinated hydrocarbon, for example, chloroform or 1,2-dichloroethane. The esterification proceeds under mild conditions if the water of reaction is removed chemically by reaction with a carbodiimide, for example, N,N'-dicyclohexylcarbodiimide, in an inert solvent such as ether, dioxane, 1,2-dimethoxyethane, benzene, CH$_2$Cl$_2$ or CHCl$_3$. A base such as pyridine can be added. Methyl and ethyl esters can also be prepared by reacting the free acids with diazomethane or diazoethane in an inert solvent such as ether, benzene or methanol.

Esters of the formula Z-Q-COOR$^3$ can be prepared by reacting metal salts of carboxylic acids Z-Q-COOH, preferably alkali metal, lead or silver salts, with halides R$^3$-Hal, preferably A-Hal. An inert solvent, for example, ether, benzene, DMF or petroleum ether, can be used.

The esterification can also be carried out in several steps by, first converting an acid to a halide Z-Q-COHal and reacting this with an alcohol A-OH or phenol Ar-OH or a corresponding metal alcoholate or metal phenolate, if appropriate, in the presence of an acid catalyst or of a base, such as NaOH, KOH, Na$_2$CO$_3$, K$_2$CO$_3$ or pyridine. Preferably, an excess of the alcohol and/or an inert solvent is used and the reaction is carried out at temperatures between 0° and the boiling point. Tert.-alkyl esters can be obtained, for example, from the acid chlorides and potassium tert.-alcoholates. Suitable solvents for this purpose are, for example, THF or benzene.

Esters of the formula Z-Q-COOR$^3$ can also be prepared by transesterifying another ester with an excess of the alcohol or phenol R$^3$-OH or by reacting a carboxylic acid of the formula Z-Q-COOH with any desired other ester of the particular alcohol or phenol of the formula R$^3$-OH, the latter ester preferably being employed in excess. The reaction is preferably carried out in the presence of a basic catalyst (for example, sodium ethylate) or an acidic catalyst (for example, sulphuric acid) at a temperature of from 0° to 120° C.

Any of the above-described esterification procedures, can also be used to prepare esters of the formula Z-Q-CH$_2$OAc from an acid of the formula AcOH or a salt, halide or anhydride thereof, and an alcohol of the formula Z-Q-CH$_2$OH or the corresponding metal alcoholate or halide. Acetates of the formula Z-Q-CH$_2$OCOCH$_3$ are preferably obtained from such alcohols by reaction with acetyl chloride or acetic anhydride and formates of the formula Z-Q-CH$_2$-O-CHO are preferably obtained by heating with excess formic acid.

In a resulting product of formula I, the Q radical can also be converted into another Q radical by treatment with a dehydrating or reducing agent.

Thus, a resulting hydroxy compound of the formula Z-C(OH)(CH$_3$)-CH$_2$-Y can be dehydrated to give the corresponding unsaturated compound of the formula Z-C(CH$_3$)=CH-Y, preferably by the action of an acid catalyst, such as hydrochloric acid, sulphuric acid or a sulphonic acid, such as p-toluenesulphonic acid, in an inert solvent, for example acetic acid or a hydrocarbon, such as benzene or toluene, at a temperature of from 0° to 150° C, preferably from 20° to 110° C, or by reaction with a dehydrating agent, such as acetic anhydride, preferably at the boil.

A hydroxy compound Z-C(OH)(CH$_3$)-CH$_2$-Y or an unsaturated compound Z-C(CH$_3$)=CH-Y can be reduced to a saturated compound of the formula Z-CH(CH$_3$)-CH$_2$-Y. Reduction of hydroxy compounds can be effected, for example, with hydriodic acid, preferably in acetic acid at temperatures between 20° and the boiling point, preferably at the boiling point. Tin-(II)chloride, preferably in acetic and/or concentrated hydrochloric acid, at 20° to 120°, preferably 120°, can be used. Hydrogenolysis, for example, on Pd at room temperature in acetic acid in the presence of a strong acid, e.g., HClO$_4$, can be used. A multi-step reduction is possible by first replacing the OH group by a chlorine atom using SOCl$_2$ and then removing the chlorine atom hydrogenolytically.

Unsaturated compounds can be hydrogenated, preferably catalytically, under conditions indicated above, for example, on a noble metal catalyst, e.g., palladium-on-charcoal, at room temperature under normal pressure, or with nascent hydrogen, as indicated above, for example, using sodium amalgam in aqueous-alcoholic medium. If an ester is the starting material, hydrolysis to the acid can take place along with reduction carried out in a strongly basic medium.

An acid Z-Q-COOH can be converted, by reaction with a base, to one of its physiologically acceptable metal or ammonium salts. Exemplary salts include, but are not limited to, sodium, potassium, magnesium, calcium, copper(II) and ammonium and substituted ammonium salts, for example, dimethylammonium, diethylammonium and diisopropylammonium salts, monoethanolammonium, diethanolammonium and triethanolammonium salts and cyclohexylammonium, dicyclohexylammonium and dibenzylethylenediammonium salts. It is also possible to use a salt of the particular metal with another acid, preferably a weak and readily volatile acid, for example, an acetate, to prepare the desired salts. Thus, to prepare copper (II) salts, acids Z-Q-COOH can be reacted with Cu(OOCCH$_3$)$_2$.

Conversely, acids Z-Q-COOH can be liberated from their metal salts and ammonium salts by treatment with acids.

Compounds of Formula I can contain a center of asymmetry and usually occur in the racemic form. The racemates can be resolved into their optical antipodes using known mechanical or chemical methods, as reported in the literature. Acids Z-Q-COOH can be resolved by forming a salt with an optically active base and the alcohols Z-Q-CH$_2$OH can be resolved by esterification with an optically active acid or by forming an acid ester, for example, a phthalate and splitting these with an optically active base.

The compounds of this invention have valuable pharmacological properties and are well tolerated. More particularly, anti-inflammatory effects can be demonstrated on rats by the Newbould, adjuvant-arthritis test, Brit. J. Pharmacol., Volume 21 (1963), pages 127–136. Other types of activity include analgesic and antipyretic effects, lowering of the lipid level, i.e. cholesterol and triglyceride level, inhibiting thrombocyte aggregation. These types of activity are demonstrated by the customary methods.

Compounds of Formula I can be used as medicaments, especially as anti-inflammatory agents for living organisms and as intermediates for the preparation of other medicaments. Compounds of Formula I (Y = COOH) can, for example, be transformed bia their acid chlorides (I, Y = COCl) to the corresponding amides (I, Y = CONH$_2$) which, in turn, can be reduced with LiAlH$_4$ to the corresponding amines (I, Y = CH$_2$NH$_2$). These can be alkylated to yield the corresponding secondary and tertiary amines, piperidines, morpholins etc.

Compounds of Formula I and their physiologically acceptable salts can be used, mixed with solids, liquid and/or semi-liquid medicinal excipients, as medicaments in human medicine or veterinary medicine. Excipients which can be used are organic or inorganic substances which are suitable for enteral or parenteral administration or topical application and which do not react with the new compounds, for example, water, vegetable oils, benzyl alcohols, polyethylene glycols, gelatine, lactose, starch, magnesium stearate, talc and white petroleum jelly. Formulations used for enteral administration are, in particular, tablets, dragees, capsules, syrups, elixirs, drops or suppositories; those used for parenteral administration are solutions, preferably oily or aqueous solutions, and also suspensions, emulsions or implants and those used for topical application are ointments, creams or powders. The new compounds can also be lyophilized and the resulting lyophilizates can be used, for example, to prepare injection formulations. The formulations indicated can be sterilized and/or contain auxiliaries, such as lubricants, preservatives, stabilizers and/or wetting agents, emulsifiers, salts for regulating the osmotic pressure, buffer substances, dyestuffs, flavorings and/or aromatic substances. They can, f desired, also contain one or more further active compounds, for example, one or more vitamins.

As a rule, the substances according to the invention are adminstered analogously to known anti-inflammatory agents which are available commercially, such as indomethacin, preferably in dosages of between about 10 and 1,000 mg. especially between 30 and 300 mg. per dosage unit. The daily dose is preferably between about 0.2 and 20 mg./kg. of body weight. However, the specific dose for each particular patient depends on diverse factors, for example, on the efficiency of the compound employed, the age, the body weight, the general state of health, the sex, the diet, the time and the route of administration, the rate of excretion, the combination of medicinal substances and the severity of the particular illness to which the therapy applies. Oral administration is preferred.

Each of the compounds of Formula I in the examples which follow is particularly suitable for the preparation of pharmaceutical formulations.

In the examples which follow "customary working up" means: water is added if necessary, the mixture is extracted with an organic solvent, such as benzene, chloroform or methylene chloride, the phases are separated, the organic phase is dried over sodium sulfate, filtered and evaporated, and the product is purified by chromatography and/or crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. 23.2 g. of 4-acetyl-2',4'-difluorobiphenyl, obtainable by reacting 2,4-difluorobiphenyl with actyl chloride in the presence of AlCl$_3$, and 11.1 ml. of ethyl bromoacetate are dissolved in a mixture of 75 ml. of benzene and 75 ml. of toluene. A 40 ml. portion of the resulting solution is added to 7 g. of zinc powder, previously washed successively with 1% hydrochloric acid, water and actone and dried and the mixture is warmed to 70° with stirring and under a nitrogen atmosphere. After the reaction has begun, the remainder of the solution is added dropwise, the mixture is heated under reflux for one hour and cooled and 40 ml. of 20% sulfuric acid are added dropwise in order to decompose the alcoholate Z-C(CH$_3$) (OZnBr)-CH$_2$-COOC$_2$H$_5$ (Z is 2',4'-difluoro-4-biphenylyl). The organic phase is separated off and worked up in the customary manner to give 3-(2',4'-difluoro-4-biphenylyl)-3-hydroxybutyric acid ethyl ester, m.p. 96°–97° C.

The following compounds are obtained analogously from the corresponding ketones by reaction with methyl or ethyl bromoacetate:

3-(2',4'-difluoro-4-biphenylyl)-3-hydroxybutyric acid methyl ester,
3-(2',4'-dichloro-4-biphenylyl)-3-hydroxybutyric acid ethyl ester,
3-(3',4'-dichloro-4-biphenylyl)-3-hydroxybutyric acid ethyl ester,
3-(2',4'-dibromo-4-biphenylyl)-3-hydroxybutyric aicd ethyl ester,
3-(p-2,4-difluorophenoxyphenyl)-3-hydroxybutyric acid ethyl ester,
3-(p-2,4-dichlorophenoxyphenyl)-3-hydroxybutyric acid ethyl ester, and
3-(p-2-fluoro-4-chlorophenoxyphenyl)-3-hydroxybutyric acid ethyl ester.

b. 10 g. of 3-(2',4'-difluoro-4-biphenylyl)-3-hydroxybutyric acid ethyl ester are dissolved in 50 ml. of ethanol and the solution is heated under reflux with 2 g. of KOH for 3 hours, evaporated and worked up in the customary manner to give 3-(2',4'-difluoro-4-biphenylyl)-3-hydroxybutyric acid, m.p. 121°–123°.

The following compounds are obtained analogously by saponification of the corresponding esters:

3-(2',4'-dichloro-4-biphenylyl)-3-hydroxybutyric acid, 3-(3',4'-dichloro-4-biphenylyl)-3-hydroxybutyric acid,
3-(2',4'-dibromo-4-biphenylyl)-3-hydroxybutyric acid,
3-(p-2,4-difluorophenoxyphenyl)-3-hydroxybutyric acid,
cyclohexylamine salt of 3-(p-2,4-dichlorophenoxyphenyl)-3-hydroxybutyric acid, m.p. 173°–174°, and
3-(p-2-fluoro-4-chlorophenoxyphenyl)-3-hydroxybutyric acid.

c. 1 g. of 3-(2',4'-difluoro-4-biphenylyl)-3-hydroxybutyric acid is dissolved in 5 ml. of acetic acid. 1 ml. of concentrated hydrochloric acid is added and the mixture is allowed to stand for 2 hours at 20° and poured onto ice. After the customary work up, 3-(2',4'-difluoro-4-biphenylyl)-2-butenoic acid, m.p. 193°–195°, is obtained.

The following compounds are obtained analogously from the corresponding hydroxy acids:
2-butenoic 3-(2',4'-dichloro-4-biphenylyl)-2 acid,
3-(3',4'-dichloro-4-biphenylyl)-2-butenoic acid,
3-(3',4'-dibromo-4-biphenylyl)-2-butenoic acid,
3-(p-2,4-difluorophenoxyphenyl)-2-butenoic acid,
3-(p-2,4-dichlorophenoxyphenyl)-2-butenoic acid, and
3-(p-2-fluoro-4-chlorophenoxyphenyl)-2-butenoic acid.

d. 1 g. of 3-(2',4'-difluoro-4-biphenylyl)-3-hydroxybutyric acid ethyl ester, or the corresponding free hydroxy acid or 3-(2',4°-difluoro-4-biphenylyl)-2-butenoic acid, is heated with 2 ml. of 67% hydriodic acid and 4 ml of acetic acid at 150° for 1 hour and the mixture is poured onto ice and decolorized with NaHSO₃ solution. After the customary work up, 3-(2',4'-difluoro-4-biphenylyl)butyric acid, m.p. 109°–110°, is obtained.

The following compounds are obtained analogously from the corresponding hydroxy esters, hydroxy acids, unsaturated esters or unsaturated acids:

3-(2',4'-dichloro-4-biphenylyl)butyric acid,
3-(3',4'-dichloro-4-biphenylyl)butyric acid
3-(2',4'-dibromo-4-biphenylyl)butyric acid,
3-(p-2,4-difluorophenoxyphenyl)butyric acid,
3-(p-2,4-dichlorophenoxyphenyl)butyric acid, and
3-(p-2-fluoro-4-chlorophenoxyphenyl)butyric acid.

e. 1 g. of 3-(2',4'-difluoro-4-biphenylyl)butyric acid in 15 ml. of methanolic hydrochloric acid is left to stand for 24 hours at 20°, evaporated and worked up in the customary manner to give 3-(2',4'-difluoro-4-biphenylyl)butyric acid methyl ester.

The corresponding methyl, ethyl, n-propyl, isopropyl, n-butyl, isobutyl, sec.-butyl, n-pentyl, isopentyl, n-hexyl, n-heptyl, n-octyl and 2-ethylhexyl esters, for example, the ethyl ester, n-propyl ester, isopropyl ester, n-butyl ester, isobutyl ester, sec.-butyl ester, n-pentyl ester, isopentyl ester, n-hexyl ester, n-heptyl ester, n-octyl ester and 2-ethylhexyl ester of 3-(2',4'-difluoro-4-biphenylyl)butyric acid; the methyl ester, ethyl ester, n-propyl ester, isopropyl ester, n-butyl ester, isobutyl ester, sec.-butyl ester, n-pentyl ester, isopentyl ester, n-hexyl ester, n-heptyl ester, n-octyl ester and 2-ethylhexyl ester of 3-(2',4'-dichloro-4-biphenylyl)butyric acid; the methyl ester, ethyl ester, n-propyl ester, isopropyl ester, n-butyl ester, isobutyl ester, sec.-butyl ester, n-pentyl ester, isopentyl ester, n-hexyl ester, n-heptyl ester, n-octyl ester and 2-ethylhexyl ester of 3-(2',4'-dibromo-4-biphenylyl) butyric acid, and the methyl ester, ethyl ester, n-propyl ester, isopropyl ester, n-butyl ester, isobutyl ester, sec.-butyl ester, n-pentyl ester, isopentyl ester, n-hexyl ester, n-heptyl ester, n-octyl ester and 2-ethylhexyl ester of 3-(p-2,4-difluorophenoxyphenyl)butyric acid; are obtained analogously after reaction times of up to 3 days from corresponding acids by reaction with HCl in methanol, ethanol, N-propanol, isopropanol, n-butanol, isobutanol, sec.-butanol, n-pentanol, isopentanol, n-hexanol, n-heptanol, n-octanol and 2-ethylhexanol, respectively.

f. 2 g. of 3-(2',4'-difluoro-4-biphenylyl)butyric acid are heated under reflux with 1 ml. of concentrated H₂SO₄ and 30 ml. of n-butanol for 7 hours. The mixture is evaporated and taken up in chloroform and the chloroform solution is washed with NaHCO₃ solution, dried and evaporated to give 3-(2',4'-difluoro-4-biphenylyl)butyric acid n-butyl ester.

g. 3.2 g. of 3-(2',4'-difluoro-4-biphenylyl)-3-hydroxybutyric acid ethyl ester are dissolved in 40 ml. of acetic acid. The solution is poured into a solution of 9 g. of SnCl₂.2H₂O in 20 ml. of concentrated hydrochloric acid. The mixture is heated under reflux for 3 hours and adjusted to pH 2 with sodium hydroxide solution. Hydrogen sulfide is passed in until no more SnS precipitates and the mixture is filtered and worked up in the customary manner to give 3-(2',4'-difluoro-4-biphenylyl)butyric acid, m.p. 109°–110°.

h. A mixture of 32 g. of 3-(2',4'-difluoro-4-biphenylyl)-3-hydroxybutyric acid ethyl ester, 8.7 g. of potassium iodide, 5.2 of red phosphorus and 45 ml. of 85% phosphoric acid is stirred and heated to 130° for 7 hours. It is worked up in the customary manner to give 3-(2',4'-difluoro-4-biphenylyl)butyric acid ethyl ester.

i. A solution of 3.2 g. of 3-(2',4'-difluoro-4-biphenylyl)-3-hydroxybutyric acid ethyl ester in 10 ml. of dichloromethane is saturated with dry HCl gas and 1 ml. of SOCl₂ is added. The mixture is warmed to 50° for 2 hours and solvent is removed. The residue, 3'(2',4'-difluoro-4-biphenylyl)-3-chlorobutyric acid ethyl ester, is dissolved in 100 ml. of methanol and hydrogenated on 100 mg. of platinum oxide under normal pressure at 25°. The precipitate is filtered off. A solution of 0.4 g. of NaOH in 5 ml. of water is added to the filtrate. The mixture is heated under reflux for 2 hours and evaporated and the residue is dissolved in water and worked up in the customary manner to give 3-(2',4'-difluoro-4-biphenylyl)-butyric acid, m.p. 109°–110°.

j. 6 g. of thionyl chloride and 10 g. of 3-(2',4'-difluoro-4-biphenylyl)butyric acid in 80 ml. of benzene are allowed to stand at 25° for 24 hours and the mixture is evaporated under reduced pressure to give 3-(2',4'-difluoro-4-biphenylyl)butyryl chloride.

k. 1 g. of crude 3-(2',4'-difluoro-4-biphenylyl)-butyryl chloride and 10 ml. of n-propanol are warmed to 95° for 3 hours and the mixture is evaporated and worked up in the customary manner to give 3-(2',4'-difluoro-4-biphenylyl)butyric acid n-propyl ester.

l. 1.12 g. of potassium tert.-butylate are added to a solution of 3 g. of crude 3-(2',4'-difluoro-4-biphenylyl)-butyryl chloride in 30 ml. of absolute THF. The mixture is stirred for 30 minutes at 20°. The precipitate is filtered off and the filtrate is evaporated and worked up in the customary manner to give 3-(2',4'-difluoro-4-biphenylyl)butyric acid tert.-butyl ester.

m. A mixture of 3 g. of crude 3-(2',4'-difluoro-4-biphenylyl)butyryl chloride, 1.73 g. of the sodium salt of p-acetamidophenol and 50 ml. of acetonitrile is stirred for one hour at 25°. The NaCl formed is filtered off and the filtrate is evaporated to give 3-(2',4'- ifluoro-4-biphenylyl)butyric acid p-acetamidophenyl ster.

n. A mixture of 2.74 g. of 3-(2',4'-difluoro-4-iphenylyl)-2-butenoic acid, 1.51 g. of p-acetamidohenol, 2.3 g. of dicyclohexylcarbodiimide and 60 ml. if THF is stirred for 24 hours.
The dicyclohexylurea formed is filtered off. The filtrate is worked up in the customary manner to give 3-(2',4'-lifluoro-4-biphenylyl)-2-butenoic acid p-acetamidopheyl ester.

o. A solution of 2.92 g. of 3-(2',4'-difluoro-4-iphenylyl)-3-hydroxybutyric acid and 0.91 g. of copier (II) acetate in 30 ml. of ethanol is evaporated to give -(2',4'-difluoro-4-biphenylyl)-3-hydroxybutyric acid Cu(II)salt.

p. A solution of 2.92 g. of 3-(2',4'-difluoro-4-iphenylyl)-3-hydroxybutyric acid in ethanol is neutralzed with an aqueous solution of 0.53 g. of $Na_2CO_3$ and vaporated to give 3-(2',4'-difluoro-4-biphenylyl)-3-lydroxybutyric acid sodium salt.

EXAMPLE 2 a. A mixture of 20 g. of ethyl bromoacetate, 26.5 g. of -acetyl-3',4'-dichlorobiphenyl and 8 lg. of zinc foil is dded to 100 ml. of benzene and the mixture is stirred nd heated under reflux for one hour. It is cooled and lilute sulfuric acid is added to decompose the alcohoate obtained. The organic phase is separated off and, fter the customary work up, 3-(3',4'-dichloro-4-iphenylyl)-3-hydroxybutyric acid ethyl ester is obained.

b. 1 g. of 3-(3+,4'-dichloro-4-biphenylyl)-3-hydrox-butyric acid ethyl ester and 0.2 g. of NaOH in 40 ml. of sopropanol are left to stand for 24 hours and the mixure is worked up to give 3-(3+,4'-dichloro-4-iphenylyl)-3-hydroxybutyric acid, m.p. 124°-126°.

c. 1 g. of 3-(3',4'-dichloro-4-biphenylyl)-3-hydrox-butyric acid and 0.1 g. of p-toluenesulfonic acid in 35 nl. of toluene are heated under reflux for 3 hours and vater by-product is removed. The reaction mixture is vorked up to give 3-(3',4'-dichloro-4-biphenylyl)-2-utenoic acid.

EXAMPLE 3

3.44 g. of 4-acetyl-2',5'-dibromobiphenyl and 1.5 g. of thyl bromoacetate are added to a mixture of 6.5 g. of granulated zinc, previously washed with dilute hydrochloric acid, water and acetone and dried, and 0.2 g. of odine in 70 ml. of benzene and 70 ml. of diethyl ether. The mixture is heated under reflux for 4 hours with occasional shaking. 5 g. of zinc and a trace of iodine are dded after 1, 2 and 3 hours, respectively, and 1.5 g. of thyl bromoacetate added after 2 hours. After cooling, cetic acid is added to decompose the resulting alcohoate and methanol is added to bring the product into olution. The mixture is poured into water and the organic phase is separated off and worked up to give -(2',4'-dibromo-4-biphenylyl)-3-hydroxybutyric acid thyl ester.

b. 1 g. of 3-(2',4'-dibromo-4-biphenylyl)-3-hydrox-butyric acid ethyl ester and 0.5 g. of potassium carbonte in 25 ml. of methanol are heated under reflux for one our and the mixture is worked up to give 3-(2',4'-libromo-4-biphenylyl)-3-hydroxybutyric acid, m.p. 118°-120°.

c. 1 g. of 3-(2',4'-dibromobiphenylyl)-3-hydrox-butyric acid and 10 ml. of acetic anhydride are heated under reflux for 2 hours and the mixture is poured onto ice and worked up in the customary manner to give 3-(2',4'-dibromo-4-biphenylyl)-2-butenoic acid.

EXAMPLE 4 a. A solution of 12.9 g. of bromoacetic acid in 50 ml. of THF is added slowly dropwise at 10°-15° to a solution of 19 g. of allyl-zinc bromide in 200 ml. of THF, prepared by reacting allyl bromide with zinc filings in THF. A solution of 23.2 g. of 4-acetyl-2',4'-difluorobiphenyl in 100 ml. of THF, 6.5 g. of zinc filings, 100 mg. of $HgI_2$ and 10.3 g. of NaBr are added to the reaction mixture, which contains an intermediate of the formula $BrCH_2$-COOZnBr, and heated under reflux until all the zinc has dissolved. After the alcholate formed has been decomposed with dilute hydrochloric acid, the mixture is worked up in the customary manner to give 3-(2',4'-difluoro-4-biphenylyl)-3-hydroxybutyric acid, m.p. 121°-123°.

b. A solution of 3.18 g. of 3-(2',4'-difluoro-4-biphenylyl)-3-hydroxybutyric acid in 30 ml. of acetic acid is hydrogenated, at 20° and under normal pressure, on 0.2 g. of 10% Pd/C in the presence of 0.01 ml. of $HClO_4$. The mixture is filtered and the filtrate is diluted with water to give 3-(2',4'-difluoro-4-biphenylyl)-butyric acid, m.p. 109°-110°.

EXAMPLE 5 a. A solution of 23.2 g. of 4-acethyl-2',4'-difluorobiphenyl in 50 ml. of THF and 50 ml. of ether is added slowly dropwise to a solution of 17.5 g. of ethoxyethinylmagnesium bromide in 200 ml. of ether, prepared by reacting ethoxyacetylene with ethyl magnesium bromide. The mixture is stirred for 1 hour at 20°. The reaction product is hydrolyzed with ice water/ammonium chloride and extracted with ether. The combined ether extracts are dried over $MgSO_4$ and evaporated. Residual 1-ethoxy-3-(2',4'-difluoro-4-biphenylyl)-butyn-3-ol is dissolved in 200 ml. of 95% ethanol and 0.05 g. of solid $CO_2$ is added to the solution and the mixture is left to stand for 12 hours at 20°. The customary work up gives 3-(2',4'-difluoro-4-biphenylyl)-2-butenoic acid ethyl ester, m.p. 54°-56°.

b. 3.02 g. of 3-(2',4'-difluoro-4-biphenylyl)-2-butenoic acid ethyl ester in 14 ml. of 1 N sodium hydroxide solution and 30 ml. of ethanol are heated under reflux for 3 hours. 40 ml. of water are added and 55 g. of 2.5% sodium amalgam are added in portions, at 25° with stirring, over the course of 5 hours. The mixture is stirred for 5 hours more and warmed on a water bath. The supernatant liquor is decanted from the mercury. Alcohol is distilled off and the reaction mixture is worked up in the customary manner to give 3-(2',4'-difluoro-4-biphenylyl)butyric acid, m.p. 109°-110°.

EXAMPLE 6 a. 3.1 g. of sodium are dissolved in 40 ml. of methanol. 20 ml. of DMF and then 25 g. of diethylphosphonoacetic acid methyl ester are added and the resulting mixture is added, at 40°-50°, to a solution of 23.2 g. of 4-acetyl-2',4'-difluorobiphenyl in 100 ml. of DMF. After stirring for 3 hours at 40°-50°, the mixture is poured onto ice and the intermediate Z-C(CH$_3$) (ONa)-CH[PO(OC$_2$H$_5$)$_2$[-COOCH$_3$ (Z is 2',4'-difluoro-4-biphenylyl), which has formed, is hydrolyzed with dilute acetic acid. The reaction mixture is worked up in the customary manner to give 3-(2',4'-diluoro-4-biphenylyl)-2-butenoic acid methyl ester, m.p. 90°-92°.

The following compounds are obtained analogously using the corresponding dialkylphosphonoalkanoic acid alkyl esters:

3-(2',4'-dichloro-4-biphenylyl)-2-butenoic acid methyl ester,
3-(3',4'-dichloro-4-biphenylyl)-2-butenoic acid methyl ester,
3-(2',4'-dibromo-4-biphenylyl)-2-butenoic acid methyl ester,
3-(p-2,4-difluorophenoxyphenyl)-2-butenoic acid methyl ester,
3-(p-2,4-dichlorophenoxyphenyl)-2-butenoic acid methyl ester,
3-(p-2-fluoro-4-chlorophenoxyphenyl)-2-butenoic acid methyl ester,
3-(2',4'difluoro-4-biphenylyl)-2-butenoic acid ethyl ester,
3-(2', 4'-dichloro-4-biphenylyl)-2-butenoic acid ethyl ester,
3-(3',4'-dichloro-4-biphenylyl)-2-butenoic acid ethyl ester,
3-(2',4'-dibromo-4-biphenylyl)-2-butenoic acid ethyl ester,
3-(p-2,4-difluorophenoxyphenyl)-2-butenoic acid ethyl ester,
3-(p-2,4-dichlorophenoxyphenyl)-2-butenoic acid ethyl ester, and
3-(p-2-fluoro-4-chlorophenoxyphenyl)-2-butenoic acid ethyl ester.

b. 1 g. of 3-(2'4'-difluoro-4-biphenylyl)-2-butenoic acid methyl ester in 20 ml. of ethanol is hydrogenated on 0.1 g. of 5% Pd-C under 1 atmosphere at 20° until the reaction has ceased. The mixture is filtered and the filtrate is evaporated to give 3-(2',4'-difluoro-4-biphenylyl)butyric acid methyl ester.

The following compounds are obtained analogously by hydrogenation of the corresponding unsaturated esters:

3-(2',4'-dichloro-4-biphenylyl)butyric acid methyl ester,
3-(3',4'-dichloro-4-biphenylyl)butyric acid methyl ester,
3-(2',4'-dibromo-4-biphenylyl)buytric acid methyl ester,
3-(p-2,4-difluorophenoxyphenyl)butyric acid methyl ester,
3-(p-2,4-dichlorophenoxyphenyl)butyric acid methyl ester,
3-(p-2-fluoro-4-chlorophenoxyphenyl)butyric acid methyl ester,
3-(2',4'-difluoro-4-biphenylyl)butyric acid ethyl ester,
3-(2',4'-dichloro-4-biphenylyl)-butryric acid ethyl ester,
3-(3',4'-dichloro-4- biphenylyl)butyric acid ethyl ester,
3-(2',4'dibromo-4-biphenylyl)butyric acid ethyl ester,
3-(p-2,4-difluorophenoxyphenyl)butyric acid ethyl ester,
3-(p-2,4-dichlorophenoxyphenyl)butyric acid ethyl ester, and
3-(p-2-fluoro-4-chlorophenoxyphenyl)butyric acid ethyl ester.

c. 3.04 g. of 3-(2',4'-difluoro-4-biphenylyl)butyric acid ethyl ester and 1 g. of KOH in 25 ml. of ethanol are heated under reflux for 2 hours. The mixture is evaporated. The residue is dissolved in water and the solution is washed with ether and acidified to pH 3 with hydrochloric acid and worked up in the customary manner to give 3-(2',4'-difluoro-4-biphenylyl)butyric acid, m.p. 109°–110°.

d. 3.04 g. of 3-(2',4'-difluoro-4-biphenylyl)butyric acid ethyl ester in a mixture of 25 ml. of acetic acid and 25 ml of 25% hydrochloric acid are heated under reflux for 90 minutes. The customary work up gives 3-(2',4'-difluoro-4-biphenylyl)butyric acid, m.p. 109°–110°.

e. A mixture of 1 g. of 3-(2',4'-difluoro-4-biphenylyl)butyric acid ethyl ester and 100 ml. of water is heated to 180° in an autoclave for 24 hours. It is cooled and worked up in the customary manner to give 3-(2',4'-difluoro-4-biphenylyl)butyric acid, m.p. 109°–110°.

EXAMPLE 7 a. A solution of 21.4 g. of lithium diisopropylamide in 200 ml. of THF is added to a stirred solution of 32 g. of α-dibenzylphosphonoacetic acid (carboxymethylphosphonic acid dibenzyl ester) in 300 ml. of THF at −80°. Then a solution of 23.2 g. of 4-acetyl-2',4'-difluorobiphenyl in 250 ml. of THF is added. The mixture is stirred for 12 hours more, during which it is allowed to come to room temperature. The product Z-C(CH$_3$) (OLi)-CH[P=O (OCH$_2$C$_6$H$_5$)$_2$]COOLi (Z is 2',4'-difluoro-4-biphenyl), which is formed, is hydrolyzed with dilute acetic acid/ice. The customary work up gives 3-(2',4'-difluoro-4-biphenylyl)-2-butenoic acid, m.p. 193°–195°.

b. 1 g. of 3-(2',4'-difluoro-4-biphenylyl)-2-butenoic acid is dissolved in 10 ml. of THF and an ethereal solution of diazomethane is added dropwise, with stirring, until no further evolution of nitrogen is observed. After 20 minutes, the mixture is evaporated to give 3-(2',4'-difluoro-4-biphenylyl)-2-butenoic acid methyl ester, m.p. 90°–92°.

c. 1 g. of 3-(2',4'-difluoro-4-biphenylyl)-2-butenoic acid is dissolved in 25 ml. of dioxane. 0.1 g. of PtO$_2$ is added and the hydrogenation is carried out at 20° under normal pressure until hydrogen absorption has ceased. The mixture is filtered and the filtrate is evaporated to give 3-(2',4'-difluoro-4-biphenylyl)butyric acid, m.p. 109°–110°.

EXAMPLE 8

69.7 g. of triphenylphosphoranylideneacetic acid ethyl ester and 29.7 g. of 4-(1-bromoethyl)-2',4'-difluorobiphenyl in 300 ml. of absolute ethyl acetate are heated under reflux for 54 hours. The precipitate is filtered off and the filtrate is evaporated. Crude [1-(2',4'-difluoro-4-biphenylyl)ethyl]triphenylphophoranylideneacetic acid ethyl ethyl ester thus obtained is dissolved in 500 ml. of methanol to which 150 ml. of 20% potassium hydroxide solution are added and the mixture is heated under reflux for one hour. The methanol is distilled off, water is added and the reaction mixture is washed with ether and acidified with hydrochloric acid to give 3-(2',4'-difluoro-4-biphenylyl)butyric acid, m.p. 109°–110°.

EXAMPLE 9

Grignard reagent obtained from 14.2 g. of methyl iodide and 2.4 g. of magnesium in 100 ml. of THF is added dropwise to a solution of 30.4 g. of 3-(2',4'-difluoro-4-biphenylyl)-3-oxopropionic acid ethyl ester, obtained by brominating 4-acetyl-2',4'-difluorobiphenyl to 4 bromacetyl-2',4'-difluorobiphenyl, reacting this with KCN to give 4-cyanoacetyl-2',4'-difluorobiphenyl, hydrolyzing the latter and esterifying the reaction product, in 200 ml. of THF. When the addition is complete, the mixture is heated and stirred for 2 hours more on a water bath and cooled. The resulting alcoholate is hydrolyzed with ice and saturated NH₄Cl solution. The ether phase is dried and evaporated to give 3-(2',4'-difluoro-4-biphenylyl)-3-hydroxybutyric acid ethyl ester, m.p. 96°–97°.

EXAMPLE 10 a. A solution of 2.62 g. of 1-(2',4'-difluoro-4-biphenylyl)-3-hydroxypropan-1-one, obtained by acylating 2,4-difluorobiphenyl with 3-methoxypropionyl chloride to give 1-(2',4'-difluoro-4-biphenylyl)-3-methoxypropan-1-one and subsequently effecting ether scission, in 20 ml. of THF is added dropwise, at 20° to stirred Grignard solution prepared from 3 g. of methyl iodide and 0.5 g. of magnesium in 100 ml. of ether. The mixture is stirred for 4 hours more and the resulting alcoholate is decomposed with water and dilute sulfuric acid. The reaction mixture is worked up in the custromary manner to give 3-(2',4'-difluoro-4-biphenylyl)butane-1,3-diol, m.p. 82°–84°.

b. Silver oxide, freshly prepared from 3.2 g. of AgNO₃ and 0.8 g. of NaOH in 25 ml. of water, is added to a mixture of 2.78 g. of 3-(2',4'-difluoro-4-biphenylyl)butane-1,3-diol and 2 g. of NaOH in 20 ml. of water. The mixture is heated under reflux for 2 hours and filtered. The filtrate is worked up in the customary manner to give 3-(2',4'-difluoro-4-biphenylyl0-3-hydroxybutyric acid, m.p. 121°–123°.

EXAMPLE 11

A solution of 2',4'-difluoro-4-biphenylylmagnesium bromide, obtained from 2.69 g. of 4-bromo-2',4'-difluorobiphenyl and 0.24 g. of magnesium in 100 ml. of ether, is added dropwise at 20° to a stirred solution of 1.3 g. of ethyl acetoacetate in 40 ml. of ether. The mixture is stirred for 2 hours more and the resulting alcoholate is decomposed with ice and saturated NH₄ Cl solution. The ether phase is dried and evaporated to give 3-(2',4'-difluoro-4-biphenylyl)-3-hydroxybutyric acid ethyl ester, m.p. 96°–97°.

EXAMPLE 12

0.44 g. of 1-hydroxy-3-butanone in 40 ml. of ether is added dropwise, at 20° stirred Grignard solution obtained from 2.69 g. of 4-bromo-2',4'-difluorobiphenyl and 0.24 g. of magnesium in 100 ml. of ether. The mixture is stirred for 2 hours more and the resulting alcoholate is decomposed with dilute sulfuric acid. The ether phase is worked up in the customary manner to give 3-(2',4'-difluoro-4-biphenylyl)butane-1,3-diol, m.p. 82°–84°.

EXAMPLE 13

2.6 g. of 3-(2',4'-difluoro-4-biphenylyl)-1-buten-3-ol, obtained from 2',4'-difluoro-4-biphenylylmagnesium bromide and methyl vinyl ketone, are dissolved in 5 ml. of diglyme. 3 ml. of a 1 molar solution of NaBH₄ in diglyme is added and a solution of 0.56 g. of BF₃ etherate in 1.2 ml. of diglyme is added dropwise under N₂. Subsequently, 0.7 ml. of water is added and then 1.4 ml. of 3 N NaOH and 1.4 ml. of 30% H₂O₂ are added dropwise at 80°–100°. The mixture is cooled. Ice water is added and the reaction mixture is worked up in the customary manner, with hydrolysis of the boric acid ester intermediate product to give 3-(2',4'-difluoro-4-biphenylyl)butane-1,3-diol, m.p. 82°–84°.

EXAMPLE 14

1 g. of 3-chloro-3-(2',4'-difluoro-4-biphenylyl)butyric acid, obtained by addition of HCl to 3-(2',4'-difluoro-4-biphenylyl)-2-butenoic acid, and 25 ml. of 20% potassium hydroxide solution are heated under reflux for 10 minutes. The mixture is cooled, washed with ether and acidified to give 3-(2',4'-difluoro-4-biphenylyl)-3-hydroxybutyric acid, m.p. 121°–123°.

EXAMPLE 15

3.55 g. of 3-(2',4'-difluoro-4-biphenylyl)-3-bromobutyric acid, obtained by brominating 3-(2',4'-difluoro-4-biphenylyl)butyric acid, are dissolved in a mixture of 15 ml. of acetone and 15 ml. of water. One drop of sulfuric acid is added and the mixture is warmed to 45° for 4 hours and worked up in the customary manner to give 3-(2',4'-difluoro-4-biphenylyl)-3-hydroxybutyric acid, m.p. 121°–123°.

EXAMPLE 16

2 g. of 3-(2',4'-difluorobiphenylyl)-3-acetoxybutyric acid, obtained from 3-(2',4'-difluoro-4-biphenylyl)-3-bromobutyric acid and potassium acetate, and 1 g. of KOH in 25 ml. of methanol are heated under reflux for 2 hours. The reaction mixture is worked up with water and chloroform to give 3-(2',4'-difluoro-4-biphenylyl)-3-hydroxybutyric acid, m.p. 121°–123°.

EXAMPLE 17

1 g. of 2-[1-(2',4'-biphenylyl)ethyl]butan-3-one acid ethyl ester, obtained by reacting 4-(1-bromoethyl)-2',4'-difluorobiphenyl with ethyl acetoacetate, and 15 ml. of 50% KOH are stirred for 45 minutes at 40° under N₂. The mixture is cooled, diluted with water and brought to pH 10 with HCl. The reaction mixture is washed with ether and worked up in the customary manner to give 3-(2',4'-difluoro-4-biphenylyl)butyric acid, m.p. 109°–110°.

EXAMPLE 18

1 g. of 3-(2',4'-difluoro-4-biphenylyl)butyronitrile, obtained from 4-(1-bromo-2-propyl)2',4'-difluorobiphenyl and KCN, in 15 ml. of ethanol and 2 ml. of water is heated under reflux with 2 g. of KOH for 40 hours. The mixture is evaporated and the residue is worked up in the customary manner to give 3-(2',4'-difluoro-4-biphenylyl)butyric acid, m.p. 109°–110°.

EXAMPLE 19

1 g. of 3-(2',4'-difluoro-4-biphenylyl)butyronitrile and 6 ml. of acetic acid and 6ml. of concentrated hydrochloric acid are heated under reflux for 2 hours under nitrogen. The mixture is evaporated. The residue is dissolved in dilute NaOH and the solution is washed with ether and worked up in the customary manner to give 3-(2',4'-difluoro-4-biphenylyl)butyric acid, m.p. 109°–110°.

EXAMPLE 20

1 g. of 3-(2',4'-difluoro-4-biphenylyl)butyronitrile, 3 ml. of n-hexanol and 0.1 g. of concentrated H₂SO₄ are heated under reflux for 48 hours. 3 ml of water are added and the mixture is heated under reflux for 48 hours more and worked up in the customary manner to give 3-(2',4'-difluoro-4-biphenylyl)butyric acid, m.p. 109°–110°.

EXAMPLE 21

1 g. of 3-(2',4'-difluoro-4-biphenylyl)butyric acid iminoethyl ether hydrochloride, obtained from 3-(2',4'-difluoro-4-biphenylyl)butyronitrile and ethanol/HCl in ether at 0°, and 25 ml. of water are heated under reflux for 1 hour. The customary work up gives 3-(2',4'-difluoro-4-biphenylyl)butyric acid ethyl ester.

EXAMPLE 22

2.76 g. of 3-(2',4'-difluoro-4-biphenylyl)butyramide, obtained from the nitrile and sulfuric acid at 25°, and 5 g. of KOH in 100 ml. of ethanol are heated under reflux under $N_2$ for 3 hours. The mixture is evaporated and worked up in the customary manner to give 3-(2',4'-difluoro-4-biphenylyl)butyric acid, m.p. 109°–110°.

EXAMPLE 23

A mixture of 1 g. of 3-(2',4'-difluoro-4-biphenylyl)butyramide, 2 ml. of concentrated hydrochloric acid and 2 ml. of acetic acid is heated under reflux for 48 hours and, after addition of water, is worked up in the customary manner to give 3-(2',4'difluoro-4-biphenylyl)butyric acid, m.p. 109°–110°.

EXAMPLE 24

3.12 g. of 1-chloro-3-p-(2,4-difluorophenoxy)phenyl-3-butanol, obtained by reacting 4-(3-chloropropionyl)-2',4'-difluorodiphenyl ether with $CH_3MgI$ and subsequently hydrolyzing the reaction product, and a solution of 2 g. of $Ba(OH)_2$ in 40 ml. of methanol are heated under reflux for 3 hours. Water is added and the product is extracted with chloroform and the extract evaporated to give 3-p-(2,4-difluorophenoxy)-phenylbutane-1,3-diol.

EXAMPLE 25 a. 2.96 g. of 1-chloro-3-(2',4'-difluoro-4-biphenylyl)-3-butanol, obtained from 2',4'-difluoro-4 biphenylyl-magnesium bromide and 1-chloro-3-butanone, are dissolved in 20 ml. of DMF. 3 g. of anhydrous potassium acetate are added and the mixture is stirred at 60° for 3 hours. The customary work up gives 1-acetoxy-3-(2',4'-difluoro-4-biphenylyl)-3-butanol.

b. A solution of 3.2 g. of 1-acetoxy-3-(2',4'-difluoro-4-biphenylyl)-3-butanol and 2 g. of NaOH in 30 ml. of 80% aqueous ethanol is heated under reflux for 3 hours. Water is added; the product is extracted with chloroform, and the extract is evaporated to give 3-(2',4'-difluoro-4-biphenylyl)butane-1,3-diol, m.p. 82°–84°.

EXAMPLE 26 a. Analogously to Example 25 (a), 3-bromo-3-(2',4'-difluoro-4-biphenylyl)butan-1-ol, obtained by brominating 3-(2',4'-difluoro-4-biphenylyl)butan-1-ol, and potassium acetate are reacted to give 3-acetoxy-3-(2',4'-difluoro-4-biphenylyl)butan-1-ol.

b. 3.20 g. of 3-acetoxy-3-(2',4'-difluoro-4-biphenylyl)-butan-1-ol and 2 g. of KOH in 50 ml. of methanol are heated under reflux for 2 hours. Water and chloroform are added and the reaction mixture is worked up to give 3(2',4'-difluoro-4-biphenylyl)butane-1,3-diol, m.p. 82°–84°.

EXAMPLE 27

A solution of 1 g. of $NaNO_2$ in 5 ml. of water is added to a solution of 2.77 g. of 1-amino-3-(2',4'-difluoro-4-biphenylyl)butan-3-ol, obtained from 3-hydroxy-3-(2',4'-difluoro-4-biphenylyl)butyramide with $LiAlH_4$, in 50 ml. of 15% aqueous acetic acid, cooled with ice. The mixture is warmed to 80° for 1 hour and worked up in the customary manner to give 3-(2',4'-difluoro-4-biphenylyl)butane-1,3-diol, m.p. 82°–84°.

EXAMPLE 28

2.92 g. of 1-methoxy-3-(2',4'-difluoro-4-biphenylyl)-butan-3-ol, obtained from 3-methoxy-1-(2',4'-difluoro-4-biphenylyl)propan-1-one and $CH_3MgI$, and a mixture of 5 ml. of 48% aqueous HBr and 5 ml. of acetic acid are heated under reflux for 2 hours. 10 ml. of 10% methanolic KOH are added and the mixture is heated under reflux again for 2 hours and worked up in the customary manner to give 3-(2',4'-difluoro-4-biphenylyl)butane-1,3-diol, m.p. 82°–84°.

EXAMPLE 29

1.2 g. of magnesium filings and 1.2 g. of magnesium powder are heated and stirred in 60 ml. of absolute ether while a moderate stream of dry $CO_2$ is introduced. A small crystal of iodine is added and a solution of 2.68 g. of 4-(1-chloro-2-propyl)-2',4'-difluorobiphenyl, obtained from 4-(1-hydroxy-2-propyl)-2',4'-difluorobiphenyl and $SOCl_2$, in 20 ml. of absolute ether is added dropwise. The mixture is heated under reflux for 20 minutes more, cooled and filtered. The filtrate is evaporated. Water is added and the reaction mixture is worked up in the customary manner to give 3-(2',4'-difluoro-4-diphenylyl)butyric acid, m.p. 109°–110°.

EXAMPLE 30

A solution of 3.11 g. of 4-(1-bromo-2-propyl)-2',4'-difluorobiphenyl in 20 ml. of THF is added slowly at 45° to a stirred mixture of 0.26 g. of magnesium powder and 20 ml. of THF. The mixture is stirred for 15 minutes more and filtered. The solution is poured onto 1 kg. of solid carbon dioxide and allowed to warm to 20°. Solvent is removed and the reaction mixture is worked up in the customary manner to give 3-(2',4'-difluoro-4-biphenylyl)butyric acid, m.p. 109°–110°.

EXAMPLE 31

2 g. of orthocarbonic acid tetraethyl ester are added to a solution of 2-(2',4'-difluoro-4-biphenylyl)-1-propyl-magnesium -bromide, prepared from 3.11 g. of 4-(1-bromo-2-propyl)-2',4'-difluorobiphenyl, in 40 ml. of THF and the mixture is stirred for 4 hours at 25°. Excess dilute hydrochloric acid is added slowly. The mixture is heated under reflux for 24 hours, allowed to cool and worked up in the customary manner to give 3-(2',4'-difluoro-4-biphenylyl)butyric acid, m.p. 109°–110°.

EXAMPLE 32

Grignard solution, prepared from 3.11 g. of 4-(1-bromo-2-propyl)-2-propyl)-2',4'-difluorobiphenyl, in 40 ml. of THF is added slowly to a solution of 1.2 g. of ethyl chloroformate in 20 ml. of THF. 15 ml. of concentrated hydrochloric acid are added. The mixture is heated under reflux for 24 hours and worked up in the customary manner to give 3-(2',4'-difluoro-4-biphenylyl)butyric acid, m.p. 109°–110°.

EXAMPLE 33

0.3 g. of paraformaldehyde is added to Grignard solution prepared from 3.11 g. of 4-(1-bromo-2-propyl)-2',4'-difluorobiphenyl and 0.26 g. of magnesium powder in 40 ml. of THF and the mixture is allowed to stand for 5 days. It is worked up in the customary manner, using ice/dilute hydrochloric acid, to give 3-(2',4'-difluoro-4-biphenyl)butan-1-ol.

EXAMPLE 34

1 g. of 3-(2',4'-difluoro-4-biphenylyl)-3-butenoic acid, obtained by reacting 3-(2',4'-difluoro-4-biphenylyl)-3-oxopropionic acid ethyl ester with triphenylphosphinemethylene and saponifying the reaction product, is dissolved in 25 ml. of ethyl acetate and hydrogenated on 0.1 g. of platinum at 20° and under 1 atmosphere until the absorption of hydrogen has ceased. The mixture is filtered and the filtrate is evaporated to give 3-(2',4'-difluoro-4-biphenyl)butyric acid, m.p. 109°–110°.

EXAMPLE 35

A solution of 2.76 g. of 3 hydroxy-3-(2',4'-difluoro-4-biphenylyl)-butanol, obtained by reacting 4-acetyl-2',4'-difluorobiphenyl with 2,2-diethoxyethyl magnesium bromide and subsequently hydrolyzing the reaction product, in 12 ml. of ethanol is added dropwise to a solution of 0.6 g. of $NaBH_4$ in 15 ml. of ethanol. The mixture is stirred for 2 hours at 20° and worked up in the customary manner to give 3-(2',4'-difluoro-4-biphenylyl)butane-1,3-diol, m.p. 82°–84°.

EXAMPLE 36

2 g. of 1-benzyloxy-3-p-(2,4-difluorophenoxy)phenyl-butan-3-ol, obtained from p-2,4-difluorophenoxyacetophenone and 2-benzyloxyethyl magnesium bromide, are dissolved in 50 ml. of methanol and hydrogenated on 0.5 g. of a 5% Pd-C catalyst at 20° and under normal pressure until the absorption of hydrogen has ceased, to give 3-p-(2,4-difluorophenoxy)phenylbutane-1,3-diol.

EXAMPLE 37

A solution of 1 g. of 3-(2',4'-difluoro-4-biphenylyl)-3-chloro-butan-1-ol, obtained from 3-(2',4'-difluoro-4-biphenylyl)butane-1,3-diol and HCl, in 25 ml. of ethyl acetate is hydrogenated on 1 g. of a 5% Pd-C catalyst at 20° and under 1 atmosphere until the reaction has ceased. The mixture is evaporated to give 3-(2',4'-difluoro-4-biphenylyl)butan-1-ol.

EXAMPLE 38

20.5 g. of 4-amino-2',4'-difluorobiphenyl are dissolved in a mixture of 25 ml. of 35% hydrochloric acid, 50 ml. of acetic acid and 120 ml. of water. The solution is cooled to 0° and 6.0 g. of $NaNO_2$ are added in portions. Subsequently, a solution of 1.5 g. of $Cu_2Cl_2$, 0.9 g. of LiCl and 100 g. of crotonic acid ethyl ester in 900 ml. of acetone is added dropwise at −10° to the stirred mixture under a $N_2$ atmosphere. The mixture is stirred for 4 hours more at 0°–5° and for 14 hours at 20° and extracted with benzene. The extract is washed and evaporated to give 20 g. of crude 2-chloro-3-(2',4'-difluoro-4-biphenylyl)-2-butenoic acid ethyl ester. This is dissolved in 250 ml. of acetic acid to which 50 g. of zinc dust are added. The mixture is stirred for 3 hours at 20° and filtered. After the customary work up, 3-(2',4'-difluoro-4-biphenylyl)-2-butenoic acid ethyl ester, m.p. 54°–56°, is obtained from the filtrate.

EXAMPLE 39

2 g. of 1-(2',4'-difluoro-4-biphenylyl)ethylmalonic acid diethyl ester, obtained by reacting 4-(1-bromoethyl)-2',4'-difluorobiphenyl with the Na salt of malonic acid diethyl ester, are heated under reflux for 3 hours with 30 ml. of 10% ethanolic KOH solution. Ethanol is distilled off. The residue is added to 60 ml. of water and the mixture is acidified to pH 4 with hydrochloric acid. 1-(2',4'-Difluoro-4-biphenylyl)ethylmalonic acid which has precipitated is filtered off, dried and dissolved in acetone and the solution is filtered and evaporated. The residue is heated to 100°–120°/20 mm until the evolution of $CO_2$ has ceased to give 3-(2',4'-difluoro-4-biphenylyl)butyric acid, m.p. 109°–110°.

EXAMPLE 40

A solution of crude 1-(2',4'-difluoro-4-biphenylyl)-ethylmalonic acid, obtained by saponifying 2 g. of 1-(2',4'-difluoro-4-biphenylyl)ethylmalonic acid diethyl ester with ethanolic KOH under $N_2$, in 20 ml. of acetic acid and 20 ml. of 15% HCl is heated under reflux under $N_2$ until evolution of $CO_2$ has ceased. After cooling, the customary work up gives 3-(2',4'-difluoro-4-biphenylyl)butyric acid, m.p. 109°–110°.

EXAMPLE 41

1 g. of 1-(2',4'-difluoro-4-biphenylyl)ethylmalonic acid monoethyl ester, obtained by partially saponifying the diethyl ester with 1 mole of KOH in ethanol and acidifying the reaction product, is heated slowly to 100°–130° at 18 mm. Hg. until evolution of $CO_2$ has ceased. 3-(2',4'-Difluoro-4-biphenylyl)butyric acid ethyl ester is obtained.

EXAMPLE 42

A mixture of 3.11 g. of 4-(1-bromo-3-propyl)-2',4'-difluorobiphenyl, 40 ml. of tert.-butanol, 2.3 g. of potassium tert.-butylate and 10 g. of nickel carbonyl is heated to 50° for 24 hours and subsequently evaporated to dryness. 40 ml. of 6N hydrochloric acid are added and the mixture is heated under reflux for 12 hours and worked up in the customary manner to give 3-(2',4'-difluoro-4-biphenylyl)butyric acid, m.p. 109°–110°.

EXAMPLE 43

4 ml. of formic acid are added over 20 minutes to a solution of 2.3 g. of 4-(2-propneyl)-2',4'-difluorobiphenyl, obtained by eliminating water from 4-(2-hydroxypropyl)-2',4'-difluorobiphenyl with polyphosphoric acid, in a mixture of 12 ml. of sulfuric acid and 8 ml. of trifluoroacetic acid. After 20 minutes more, the mixture is poured into water to give 3-(2',4'-difluoro-4-biphenylyl)butyric acid, m.p. 109°–110°.

EXAMPLE 44

2.48 g. of 2-(2',4'-difluoro-4-biphenylyl)propanol, or 2.3 g. of 4-propenyl-2',4'-difluorobiphenyl, is dissolved in 10 ml. of 3% ethanolic hydrochloric acid. 20 mg. of $[(C_6H_5)_3P]_2PdCl_2$ are added and the mixture is heated under 500 atmospheres of CO in an autoclave to 85° for 5 hours. After cooling, the customary work up gives 3-(2',4'-difluoro-4-biphenylyl)butyric acid ethyl ester.

EXAMPLE 45

A mixture of 2.3 g. of 4-propenyl-2',4'-difluorophenyl, or 2.48 g. of 2-(2',4'-difluoro-4-biphenylyl)propanol, 2 ml. of nickel carbonyl, 2 ml. of concentrated hydrochloric acid and 20 ml. of acetone is heated to 50° for 12 hours and irradiated with the light from a mercury vapor lamp. The mixture is evaporated to dryness and the residue is extracted with ether and worked up in the customary manner to give 3-(2',4'-difluoro-4-biphenylyl)butyric acid, m.p. 109°–110°.

EXAMPLE 46

A mixture of 2.4 g. of 2,4-difluoroiodobenzene and 2.4 g. of the disodium salt of 3-p-hydroxyphenyl-3-hydroxybutyric acid, obtained by reacting p-hydroxyacetophenone with ethyl bromoacetate and zinc and subsequently saponifying the reaction product, is warmed, in the presence of 1 g. of Cu powder in 10 ml. of HMPT, to 90° for 8 hours and worked up in the customary manner to give 3-p-(2,4-difluorophenoxy)phenyl-3-hydroxybutyric acid.

3-p-(2,4-Difluorophenoxy)phenylbutane-1,3-diol is obtained analogously from the Na salt of 3-p-hydroxyphenylbutane-1,3-diol, obtained by reducing 3-p-hydroxyphenyl-3-phydroxybutyric acid ethyl ester.

EXAMPLE 47

A solution of 3.28 g. of the sodium salt of 3-p-diodophenyl-3-hydroxybutyric acid and 1.52 g. of sodium 2,4-difluorophenolate in 20 ml. of DMF is warmed to 130° for 8 hours. The customary work up gives 3-p-(2,4-difluorophenoxy)phenyl-3-hydroxybutyric acid.

3-p-(2,4-Difluorophenoxy)phenylbutane-1,3-diol is obtained analogously from 3-p-iodophenylbutane-1,3-diol, obtained by reducing 3-p-iodophenyl-3-hydroxybutyric acid ethyl ester.

EXAMPLE 48

3 ml. of concentrated hydrochloric acid are added, at 0°, to 3.3 g. of 3-p-(2,4-diaminophenoxy)phenyl-3-hydroxybutyric acid ethyl ester, obtained by a Reformatsky reaction from p-2,4-diacetamidophenoxyacetophenone. Then a solution of 1.4 g. of $NaNO_2$ in 6 ml. of water is added at 0° to the stirred mixture. After addition of a solution of 0.7 g. of boric acid 1.5 g. of 60% hydrofluoric acid, the mixture is stirred for 40 minutes and filtered. The product is washed with water, methanol and ether and dried. The diazonium salt is heated to about 150° until decomposition is complete to give 3-p-(2,4-difluorophenoxy)phenyl-3-hydroxybutyric acid ethyl ester.

3-p-(2,4-Difluorophenoxy)phenylbutane-1,3-diol is obtained analogously from 3-p-(2,4-diaminophenoxy)phenylbutane-1,3-diol, obtained by hydrogenation of 3-(2,4-dinitrophenoxy)-phenyl-3-hydroxybutyric acid ethyl ester on $CuCr_2O_4$.

EXAMPLE 49

3.3 g. of 3-p-(2,4-diaminophenoxy)phenyl-3-hydroxybutyric acid ethyl ester are dissolved in 30 ml. of 10% hydrochloric acid. 0.7 g. of $NaNO_2$ in 2 ml. of water is added at 0°–5°. The resulting diazonium salt solution is added slowly dropwise to a hot solution of $Cu_2Cl_2$, obtained by reducing 2.1 g. of copper sulfate with $SO_2$ in 13 ml. of water in the presence of 2.6 g. of NaCl. The mixture is heated to 90°–95° for 30 minutes more, cooled and worked up in the customary manner to give 3-p-(2,4-dichlorophenoxy)phenyl-3-hydroxybutyric acid ethyl ester.

Analogously, 3-p-(2,4-dibromophenoxy)phenyl-3-hydroxybutyric acid ethyl ester is obtained using $Cu_2Br_2$ and 3-p-(2,4-dichlorophenoxy)phenylbutane-1,3-diol is obtained from 3-p-(2,4-diaminophenoxy)phenylbutane-1,3-diol and $Cu_2Cl_2$.

EXAMPLE 50 a. A solution of 32 g. of 3-(2',4'-difluoro-4-biphenylyl)-3-hydroxybutyric acid ethyl ester in 300 ml. of absolute THF is added dropwise, under nitrogen, to a suspension of 4.6 g. of $LiAlH_4$ in 200 ml. of THF and the mixture is heated under reflux for one hour. After cooling, ethyl acetate, water and 32% sodium hydroxide solution are added and the mixture is worked up in the customary manner to give 3-(2',4'-difluoro-4-biphenylyl)butane-1,3-diol, m.p. 82°–84°.

The following compounds are obtained analogously to reduction of the corresponding esters:

3-(2',4'-difluoro-4-biphenylyl)butan-1-ol,
3-(2',4'-dichloro-4-biphenylyl)butan-1-ol,
3-(2',4'-dichloro-4-biphenylyl)butane-1,3-diol,
3-(3',4'-dichloro-4-biphenylyl)butan-1-ol,
3-(3',4'-dichloro-4-biphenylyl)butane-1,3-diol,
3-(2',4'-dibromo-4-biphenylyl)butan-1-ol,
3-(2',4'-dibromo-4-biphenylyl)butane-1,3-diol, m.p. 118°–120°
3-(p-2,4-difluorophenoxyphenyl)butan-1-ol,
3-(p-2,4-difluorophenoxyphenyl)butane-1,3-diol,
3-(p-2,4-dichlorophenoxyphenyl)butan-1-ol,
3-(p-2,4-dichlorophenoxyphenyl)butane-1,3-diol,
3-(p-2-fluoro-4-chlorophenoxyphenyl)butan-1-ol, and
3-(p-2-fluoro-4-chlorophenoxyphenyl)butane-1,3-diol.

b. A mixture of 3 g. of 3-(2',4'-difluoro-4-biphenyl)butane-1,3-diol, 5 ml. of acetic anhydride and 8 ml. of pyridine is allowed to stand for 15 hours at 20°, poured into ice water and worked up with chloroform and water to give 1-acetoxy-3-(2',4'-difluoro-4-biphenylyl)butan-3-ol.

The following compounds are obtained analogously by acetylating the corresponding alcohols:

1-acetoxy-3-(2',4'-difluoro-4-biphenylyl)butane,
1-acetoxy-3-(2',4'-dichloro-4-biphenylyl)butane,
1-acetoxy-3-(2',4'-dichloro-4-biphenylyl)-butan-3-ol,
1-acetoxy-3-(3',4'-dichloro-4-biphenylyl)butane,
1-acetoxy-3-(3',4'-dichloro-4-biphenylyl)butan-3-ol,
1-acetoxy-3-(2',4'-dibromo-4-biphenylyl)butane,
1-acetoxy-3-(2',4'-dibromo-4-biphenylyl)butan-3-ol,
1-acetoxy-3-(p-2,4-difluorophenoxyphenyl)butane,
1-acetoxy-3-(p-2,4-difluorophenoxyphenyl)butan-3-ol,
1-acetoxy-3-(p-2,4-dichlorophenoxyphenyl)butane,
1-acetoxy-3-(p-2,4-dichlorophenoxyphenyl)butan-3-ol,
1-acetoxy-3-(p-2-fluoro-4-chlorophenoxyphenyl)butane,
1-acetoxy-3-(p-2-fluoro-4-chlorophenoxyphenyl)butan-3-ol.

c. Analogously to (b), the corresponding propionates, butyrates, isobutyrates, valerates, isovalerates, trimethylacetates, caproates, isocaproates, tert.-butylacetates and octanoates, for example, 1-propionyloxy-3-(2',4'-difluoro-4-biphenylyl)butan-3-ol, 1-butyryloxy-3-(2',4'-difluoro-4-biphenylyl)butan-3-ol,
1-isobutyryloxy-3-(2',4'-difluoro-4-biphenylyl)butan-3-ol,
1-valeryloxy-3-(2',4'-difluoro-4-biphenylyl)butan-3-ol,
1-isovaleryloxy-3-(2', 4'-difluoro-4-biphenylyl)butan-3-ol,
1-trimethylacetoxy-3-(2',4'-difluoro-4-biphenylyl)-butan-3-ol,
1-capronyloxy-3-(2',4'-difluoro-4-biphenylyl)butan-3-ol,
1-isocapronyloxy-3-(2',4'-difluoro-4-biphenylyl)butan-3-ol,
1-tert.-butylacetoxy-3-(2',4'-difluoro-4-biphenylyl)-butan-3-ol, and
1-octanoyloxy-3-(2',4'-difluoro-4-biphenylyl)butan-3-ol, are obtained using the corresponding anhydrides.

d. 3 g. of 3-(2',4'-difluoro-4-biphenylyl)butane-1,3-diol and 15 ml. of formic acid are warmed to 80° for 2 hours. The mixture is cooled and worked up in the customary manner to give 1-formyloxy-3-(2',4'-difluoro-4-biphenylyl)butan-3-ol.

e. 2.78 g. of 3-(2',4'-difluoro-4-biphenylyl)butane-1,3-diol are dissolved in 30 ml. of acetic acid and hydrogenated at 20° and under 1 atmosphere on 0.5 g of 10% Pd-C until the reaction has ceased. Filtering and evaporating gives 3-(2',4'-difluoro-4-biphenylyl)butan-1-ol.

EXAMPLE 51

33.4 ml. of a 70% solution of $NaAl(OCH_2CH_2OCH_3)_2H_2$ in benzene is added dropwise to a stirred mixture of 28.8 g. of 3-(2',4'-difluoro-4-biphenylyl)-2-butenoic acid methyl ester and 100 ml. of benzene and the reaction mixture is stirred overnight at 80°. The mixture is poured into 130ml. of 20% $H_2SO_4$, stirred for one hour and worked up in the customary manner to give 3-(2',4'-difluoro-4-biphenylyl)2-buten-1-ol.

The following compounds are obtained analogously by reduction of the corresponding esters:
p0 3-(2',4'-dichloro-4-biphenylyl)-2-buten-1-ol,
3-(3',4'-dichloro-4-biphenylyl)-2-buten-1-ol,
3-(2',4'-dibromo-4-biphenylyl)-2-buten-1-ol,
3-(p-2,4-difluorophenoxyphenyl)-2-buten-1-ol,
3-(p-2,4-dichlorophenoxyphenyl)-2-buten-1-ol, and
3-(p-2-flouro-4-chlorophenoxyphenl)-2-buten-1ol.

The examples given below relate to pharmaceutical formulations which contain compounds of Formula I or their salts:

EXAMPLE A: Tablets

A mixture of 1 kg. of the sodium salt of 3-(2',4'-difluoro-4-biphenylyl)-3-hydroxybutyric acid, 4 kg. of lactose, 1.2 kg. of maize starch, 0.2 kg. of talc and 0.1 kg. of magnesium stearate is pressed in the customary manner to give tablets, each of which contains 100 mg. of active compound.

EXAMPLE B: Dragees

Tablets are pressed analogously to Example A and subsequently are coated in the customary manner with coating consisting of sucrose, maize starch, talc, tragacanth and a dyestuff.

EXAMPLE C: Capsules 5 kg. of 3-(p-2,4-dichlorophenoxyphenyl)-2-butenoic acid are filled into hard gelatin capsules in the customary manner so that each capsule contains 250 mg. of active compound.

Tablets, dragees and capsules which contain one or more of the other active compounds of Formula I and-/or their physiologically acceptable salts are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An araliphatic dihalogen compound of the formula

Z-Q-Y wherein Z is

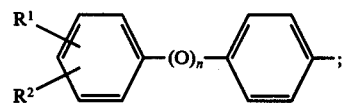

$R^1$ and $R^2$ are F, Cl or Br; Q is $—CH(CH_3)—CH_2—$, $—C(OH)(CH_3)—CH_2—$ or $—C(CH_3)=CH—$; Y is $CH_2OH$ and; $n$ is 0 or 1.

2. A compound of claim 1, wherein $n$ is 0.
3. A compound of claim 1, wherein $n$ is 1.
4. A compound of claim 1, wherein $R^1$ and $R^2$ are F.
5. A compound of claim 1, wherein Z is 2',4'-dibromo-4-biphenylyl.
6. A compound of claim 1, wherein Z is 4-(2,4-difluorophenoxy)phenyl, 4-(2,4-dichlorophenoxy)phenyl or 4-(2-fluoro-4-chlorophenoxy)phenyl.
7. A compound of claim 1, wherein Z is 2',4'-dichloro-4-biphenylyl.
8. A compound of claim 1, wherein Z is 4-(2,4-difluorophenoxy)phenyl.
9. A compound of claim 1, wherein Z is 2',4'-difluoro-4-biphenylyl.
10. A compound of claim 1, wherein Q is $—CH(CH_3)-CH_2—$.
11. A compound of claim 1, wherein Q is $—C(OH)(CH_3)-CH_2—$.
12. A compound of claim 1, wherein Q is $—C(CH_3)=CH—$.
13. 3-(2',4'-Dichloro-4-biphenylyl)butane-1,3-diol, a compound of claim 1.
14. 3-(2',4'-Dibromo-4-biphenylyl)-butane-1,3-diol, a compound of claim 1.
15. An anti-inflammatory pharmaceutical composition comprising an anti-inflammatorily effective amount per unit dosage of a compound of claim 1, in admixture with a pharmaceutically-acceptable carrier.
16. The composition of claim 15, wherein the compound is 3-(2',4'-difluoro-4-biphenylyl)butane-1,3-diol.
17. The composition of claim 15, wherein the compound is 3-(p-2,4-dichlorophenoxyphenyl)-butane-1,3-diol.
18. A method of relieving inflammation in a patient afflicted therewith comprising administering to the patient an anti-flammatorily effective amount of a compound of claim 1, in admixture with a pharmaceutically-acceptable carrier.
19. The method of claim 18, wherein the compound is administered orally.
20. The method of claim 18, wherein the effective amount is a daily dose of 0.2–20 mg./kg. of body weight.

* * * * *

UNITED STATES PATENT AND TRADEMARK OFFICE
CERTIFICATE OF CORRECTION

PATENT NO. : 4,057,647

DATED : November 8, 1977

INVENTOR(S) : JOACHIM GANTE ET AL.

It is certified that error appears in the above-identified patent and that said Letters Patent are hereby corrected as shown below:

Add the following claim:

-- 21. 3-(2',4'-Difluoro-4-biphenylyl)butane-1,3-diol, a compound of Claim 1. --.

Signed and Sealed this

Twenty-fourth Day of October 1978

[SEAL]

Attest:

RUTH C. MASON
Attesting Officer

DONALD W. BANNER
Commissioner of Patents and Trademarks